(12) United States Patent
Andre et al.

(10) Patent No.: US 7,378,249 B2
(45) Date of Patent: May 27, 2008

(54) TREATMENT OF CANCER USING TLR3 AGONISTS

(75) Inventors: Fabrice Andre, Paris (FR); Laurence Zitvogel, Antony (FR); Jean-Christophe Sabourin, Paris (FR)

(73) Assignee: Institut Gustave Roussy, Villejuif (FR)

( * ) Notice: Subject to any disclaimer, the term of this patent is extended or adjusted under 35 U.S.C. 154(b) by 52 days.

(21) Appl. No.: 11/144,322

(22) Filed: Jun. 3, 2005

(65) Prior Publication Data
US 2006/0110746 A1 May 25, 2006

Related U.S. Application Data

(63) Continuation-in-part of application No. PCT/IB2004/004093, filed on Nov. 19, 2004.

(51) Int. Cl.
G01N 33/53 (2006.01)
(52) U.S. Cl. ........................................................ 435/7.1
(58) Field of Classification Search ...................... None
See application file for complete search history.

(56) References Cited

U.S. PATENT DOCUMENTS

| | | | |
|---|---|---|---|
| 3,666,646 A | 5/1972 | Lampson et al. | |
| 4,946,778 A | 8/1990 | Ladner et al. | |
| 5,298,614 A | 3/1994 | Yano et al. | |
| 5,677,171 A * | 10/1997 | Hudziak et al. | 435/7.23 |
| 6,780,429 B1 | 8/2004 | Matsuyama et al. | |
| 2003/0165479 A1 | 9/2003 | Velleca et al. | |
| 2003/0166001 A1 | 9/2003 | Lipford et al. | |
| 2004/0121348 A1 * | 6/2004 | Kreutzer et al. | 435/6 |
| 2006/0134128 A1 | 6/2006 | Seya et al. | |
| 2006/0147456 A1 * | 7/2006 | Lebecque et al. | 424/155.1 |

FOREIGN PATENT DOCUMENTS

| | | |
|---|---|---|
| EP | 113162 | 7/1989 |
| EP | 281380 | 11/1995 |
| EP | 1 577 383 A1 | 9/2005 |
| WO | WO 98/50547 | 11/1998 |
| WO | WO 01/90151 A2 | 11/2001 |
| WO | WO 03/31573 | 4/2003 |
| WO | WO 03/031573 A2 * | 4/2003 |
| WO | WO 2004/053057 | 6/2004 |
| WO | WO 2004/053452 | 6/2004 |
| WO | WO 2004/094671 | 11/2004 |
| WO | WO 2006/010838 A2 | 2/2006 |
| WO | WO 2006/014653 A1 | 2/2006 |

OTHER PUBLICATIONS

Schmidt et al (J. Immunol., 1/4, 172(1): 138-143).*
Tockman et al (Cancer Res., 1992, 52:2711s-2718s).*
Gura (Science, 1997, 278:1041-1042.).*
Alberts et al. (Molecular Biology of the Cell, 3rd edition, 1994, p. 465).*
Lewin, B. also teaches (Genes VI, Oxford University Press, Inc., NY, Chapter 29, 1997).*
Fu et al (EMBO Journal, 1996, vol. 15, pp. 4392-4401).*
Mallampalli et al. (Biochem. J. vol. 318, 1996, pp. 333-341).*
Greenbaum et al. (Genome Biology, 2003, vol. 4, Issue 9, pp. 117.1-117.8).*
Andre et al (Journal of Clinical Oncology, Jul. 15, 2004, 22(14s): 9619).*
Yakes et al (Cancer Research, 62:4132-4141, 2002).*
Alexopoulou, L. et al. "Recognition of double-stranded RNA and activation of NF-κB by toll-like receptor 3", *Nature*, Oct. 18, 2001, pp. 732-738, vol. 413.
Chaturvedi, S. et al. "Stabilization of triple-stranded oligonculeotide complexes: use of probes containing alternating phosphodiester and stereo-uniform cationic phosphoramidate linkages", *Nucleic Acids Research*, 1996, pp. 2318-2323, vol. 24, No. 12.
Field, A. et al. "Inducers of interferon and host resistance, IV. Double-stranded replicative form (MS2-RF-RNA) from *E. coli* infected with MS2 coliphage", *Proc. Natl. Acad. Sci. U. S. A.*, Nov. 1967, pp. 2102-2108, vol. 58, No. 5.
Field, A. et al. "Inducers of interferon and host resistance, II. Multistranded synthetic polynucleotide complexes", *Proc. Natl. Acad. Sci. U. S. A.*, Sep. 1967, pp. 1004-1010, vol. 58, No. 3.
Field, A. et al. "Inducers of interferon and host resistance, V. In vitro studies", *Proc. Natl. Acad. Sci. U. S. A.*, Sep. 1968, pp. 340-346, vol. 61, No. 1.
Gil, J. et al. "Induction of apoptosis by double-stranded-RNA-dependent protein kinase (PKR) involves the α subunit of eukaryotic translation initiation factor 2 and NF-κB", *Molecular and Cellular Biology*, Jul. 1999, pp. 4653-4663, vol. 19, No. 7.
Kandimalla, E.R. et al. "Divergent synthetic nucleotide motif recognition pattern: design and development of potent immunomodulatory oligodeoxyribnucleotide agents with distinct cytokine induction profiles", *Nucleic Acids Research*, 2003, pp. 2393-2400, vol. 31, No. 9.
Niwa, M. et al. "A role for presenilin-1 in nuclear accumulation of Ire1 fragments and induction of the mammalian unfolded protein response", *Cell*, Dec. 23, 1999, pp. 691-702, vol. 99.
Peyrottes, S. et al. "Oligodeoxynucleoside phosphoramidates (P-NH$_2$): synthesis and thermal stability of duplexes with DNA and RNA targets", *Nucleic Acids Research*, 1996, pp. 1841-1848, vol. 24, No. 10.
Tytell, A. et al. "Inducers of interferon and host resistance, III. Double-stranded RNA from reovirus type 3 virions (REO 3-RNA)", *Proc. Natl. Acad. Sci. U. S. A.*, Oct. 1967, pp. 1719-1722, vol. 58, No. 4.
Adams, M. et al. "The rationale for combined chemo/immunotherapy using a Toll-like receptor 3 (TRL3) agonist and tumour-derived exosomes in advanced ovarian cancer", *Vaccine*, 2005, pp. 2374-2378, vol. 23.

(Continued)

*Primary Examiner*—Misook Yu
*Assistant Examiner*—Sean E Aeder
(74) *Attorney, Agent, or Firm*—Saliwanchik, Lloyd & Saliwanchik

(57) ABSTRACT

The present invention relates generally to the fields of genetics and medicine. More specifically, the present invention relates to improved methods of treating cancers using a TLR3 agonist, by assessing the expression of a TLR3 receptor by cancer cells.

12 Claims, 3 Drawing Sheets
(1 of 3 Drawing Sheet(s) Filed in Color)

OTHER PUBLICATIONS

Andre, F. et al. "Targeting Toll like receptor 3 by double standard RNA in breast cancer: Results from in vitro studies and randomized trial", *J. Clinical Oncology*, Jul. 15, 2004, p. 9619, vol. 22, No. 14S, XP009051335.

Cho, C. H. et al. "Monophosphoryl lipid A, Polyadenylic-polyuridylic Acid Cisplatin" *J. Korean Soc. Microbiol*, 1994, pp. 231-244, vol. 29, No. 2.

Khan, A. et al. "Polyadenylic-polyuridylic acid enhances the natural cell-mediated cytotoxicity in patients with breast cancer undergoing mastectomy", *Surgery*, Sep. 1995, pp. 531-538, vol. 118, No. 3.

Salazar, A. M. et al. "Long term treatment of malignant gliomas with intramusculary administered polyinosinic-polycytidylic acid stabilized with polylysine and carboxymethylcellulose: an open pilot study" *Neurosurgery*, Jun. 1996, pp. 1096-1104, vol. 38, No. 6.

Wen, L. et al. "The Effect of Innate Immunity on Autoimmune Diabetes and the Expression of Toll-Like Receptors on Pancreatic Islets", *The Journal of Immunology*, 2004, pp. 3173-3180, vol. 172.

Whitmore, M. et al. "Synergistic Activation of Innate Immunity by Double-Stranded RNA and CpG DNA Promotes Enhanced Antitumor Activity", *Cancer Research*, Aug. 15, 2004, pp. 5850-5860, vol. 64.

Youn, J. et al. "Adjuvant Treatment of Operable Stomach Cancer with Polyadenylic Polyuridylic Acid in Addition to Chemotherapeutic Agents: A Preliminary Report", *Int. J. Immunopharmac.*, 1990, pp. 289-295, vol. 12, No. 3.

Field, A. K. et al. "Invited Discussions: Double-Stranded Polynucleotides as Interferon Inducers" *J. Gen. Physiol.*,. 1970, pp. 90s-96s, vol. 56.

\* cited by examiner

SEQUENCE LISTING

<160> NUMBER OF SEQ ID NOS: 4

<210> SEQ ID NO 1
<211> LENGTH: 3057
<212> TYPE: DNA
<213> ORGANISM: Homo sapiens
<220> FEATURE:
<221> NAME/KEY: misc_feature
<222> LOCATION: (1)..(3057)
<223> OTHER INFORMATION: See NCBI Accession No. NM_003265
<220> FEATURE:
<221> NAME/KEY: misc_feature
<222> LOCATION: (1)..(3057)
<223> OTHER INFORMATION: TLR3 mRNA sequence
<220> FEATURE:
<221> NAME/KEY: CDS
<222> LOCATION: (102)..(2816)

<400> SEQUENCE: 1

```
cactttcgag agtgccgtct atttgccaca cacttccctg atgaaatgtc tggatttgga      60
ctaaagaaaa aaggaaaggc tagcagtcat ccaacagaat c atg aga cag act ttg     116
                                              Met Arg Gln Thr Leu
                                                1               5 cct tgt atc tac ttt tgg ggg ggc ctt ttg ccc ttt ggg atg ctg tgt       164
Pro Cys Ile Tyr Phe Trp Gly Gly Leu Leu Pro Phe Gly Met Leu Cys
             10                  15                  20 gca tcc tcc acc acc aag tgc act gtt agc cat gaa gtt gct gac tgc       212
Ala Ser Ser Thr Thr Lys Cys Thr Val Ser His Glu Val Ala Asp Cys
         25                  30                  35 agc cac ctg aag ttg act cag gta ccc gat gat cta ccc aca aac ata       260
Ser His Leu Lys Leu Thr Gln Val Pro Asp Asp Leu Pro Thr Asn Ile
     40                  45                  50 aca gtg ttg aac ctt acc cat aat caa ctc aga aga tta cca gcc gcc       308
Thr Val Leu Asn Leu Thr His Asn Gln Leu Arg Arg Leu Pro Ala Ala
 55                  60                  65 aac ttc aca agg tat agc cag cta act agc ttg gat gta gga ttt aac       356
Asn Phe Thr Arg Tyr Ser Gln Leu Thr Ser Leu Asp Val Gly Phe Asn
 70                  75                  80                  85 acc atc tca aaa ctg gag cca gaa ttg tgc cag aaa ctt ccc atg tta       404
Thr Ile Ser Lys Leu Glu Pro Glu Leu Cys Gln Lys Leu Pro Met Leu
                 90                  95                 100 aaa gtt ttg aac ctc cag cac aat gag cta tct caa ctt tct gat aaa       452
Lys Val Leu Asn Leu Gln His Asn Glu Leu Ser Gln Leu Ser Asp Lys
            105                 110                 115 acc ttt gcc ttc tgc acg aat ttg act gaa ctc cat ctc atg tcc aac       500
Thr Phe Ala Phe Cys Thr Asn Leu Thr Glu Leu His Leu Met Ser Asn
        120                 125                 130 tca atc cag aaa att aaa aat aat ccc ttt gtc aag cag aag aat tta       548
Ser Ile Gln Lys Ile Lys Asn Asn Pro Phe Val Lys Gln Lys Asn Leu
    135                 140                 145 atc aca tta gat ctg tct cat aat ggc ttg tca tct aca aaa tta gga       596
Ile Thr Leu Asp Leu Ser His Asn Gly Leu Ser Ser Thr Lys Leu Gly
150                 155                 160                 165 act cag gtt cag ctg gaa aat ctc caa gag ctt cta tta tca aac aat       644
Thr Gln Val Gln Leu Glu Asn Leu Gln Glu Leu Leu Leu Ser Asn Asn
                170                 175                 180 aaa att caa gcg cta aaa agt gaa gaa ctg gat atc ttt gcc aat tca       692
Lys Ile Gln Ala Leu Lys Ser Glu Glu Leu Asp Ile Phe Ala Asn Ser
            185                 190                 195 tct tta aaa aaa tta gag ttg tca tcg aat caa att aaa gag ttt tct       740
Ser Leu Lys Lys Leu Glu Leu Ser Ser Asn Gln Ile Lys Glu Phe Ser
```

-continued

```
                200                 205                 210
cca ggg tgt ttt cac gca att gga aga tta ttt ggc ctc ttt ctg aac      788
Pro Gly Cys Phe His Ala Ile Gly Arg Leu Phe Gly Leu Phe Leu Asn
    215                 220                 225 aat gtc cag ctg ggt ccc agc ctt aca gag aag cta tgt ttg gaa tta      836
Asn Val Gln Leu Gly Pro Ser Leu Thr Glu Lys Leu Cys Leu Glu Leu
230                 235                 240                 245 gca aac aca agc att cgg aat ctg tct ctg agt aac agc cag ctg tcc      884
Ala Asn Thr Ser Ile Arg Asn Leu Ser Leu Ser Asn Ser Gln Leu Ser
                250                 255                 260 acc acc agc aat aca act ttc ttg gga cta aag tgg aca aat ctc act      932
Thr Thr Ser Asn Thr Thr Phe Leu Gly Leu Lys Trp Thr Asn Leu Thr
            265                 270                 275 atg ctc gat ctt tcc tac aac aac tta aat gtg gtt ggt aac gat tcc      980
Met Leu Asp Leu Ser Tyr Asn Asn Leu Asn Val Val Gly Asn Asp Ser
        280                 285                 290 ttt gct tgg ctt cca caa cta gaa tat ttc ttc cta gag tat aat aat     1028
Phe Ala Trp Leu Pro Gln Leu Glu Tyr Phe Phe Leu Glu Tyr Asn Asn
    295                 300                 305 ata cag cat ttg ttt tct cac tct ttg cac ggg ctt ttc aat gtg agg     1076
Ile Gln His Leu Phe Ser His Ser Leu His Gly Leu Phe Asn Val Arg
310                 315                 320                 325 tac ctg aat ttg aaa cgg tct ttt act aaa caa agt att tcc ctt gcc     1124
Tyr Leu Asn Leu Lys Arg Ser Phe Thr Lys Gln Ser Ile Ser Leu Ala
                330                 335                 340 tca ctc ccc aag att gat gat ttt tct ttt cag tgg cta aaa tgt ttg     1172
Ser Leu Pro Lys Ile Asp Asp Phe Ser Phe Gln Trp Leu Lys Cys Leu
            345                 350                 355 gag cac ctt aac atg gaa gat aat gat att cca ggc ata aaa agc aat     1220
Glu His Leu Asn Met Glu Asp Asn Asp Ile Pro Gly Ile Lys Ser Asn
        360                 365                 370 atg ttc aca gga ttg ata aac ctg aaa tac tta agt cta tcc aac tcc     1268
Met Phe Thr Gly Leu Ile Asn Leu Lys Tyr Leu Ser Leu Ser Asn Ser
    375                 380                 385 ttt aca agt ttg cga act ttg aca aat gaa aca ttt gta tca ctt gct     1316
Phe Thr Ser Leu Arg Thr Leu Thr Asn Glu Thr Phe Val Ser Leu Ala
390                 395                 400                 405 cat tct ccc tta cac ata ctc aac cta acc aag aat aaa atc tca aaa     1364
His Ser Pro Leu His Ile Leu Asn Leu Thr Lys Asn Lys Ile Ser Lys
                410                 415                 420 ata gag agt gat gct ttc tct tgg ttg ggc cac cta gaa gta ctt gac     1412
Ile Glu Ser Asp Ala Phe Ser Trp Leu Gly His Leu Glu Val Leu Asp
            425                 430                 435 ctg ggc ctt aat gaa att ggg caa gaa ctc aca ggc cag gaa tgg aga     1460
Leu Gly Leu Asn Glu Ile Gly Gln Glu Leu Thr Gly Gln Glu Trp Arg
        440                 445                 450 ggt cta gaa aat att ttc gaa atc tat ctt tcc tac aac aag tac ctg     1508
Gly Leu Glu Asn Ile Phe Glu Ile Tyr Leu Ser Tyr Asn Lys Tyr Leu
    455                 460                 465 cag ctg act agg aac tcc ttt gcc ttg gtc cca agc ctt caa cga ctg     1556
Gln Leu Thr Arg Asn Ser Phe Ala Leu Val Pro Ser Leu Gln Arg Leu
470                 475                 480                 485 atg ctc cga agg gtg gcc ctt aaa aat gtg gat agc tct cct tca cca     1604
Met Leu Arg Arg Val Ala Leu Lys Asn Val Asp Ser Ser Pro Ser Pro
                490                 495                 500 ttc cag cct ctt cgt aac ttg acc att ctg gat cta agc aac aac aac     1652
Phe Gln Pro Leu Arg Asn Leu Thr Ile Leu Asp Leu Ser Asn Asn Asn
            505                 510                 515 ata gcc aac ata aat gat gac atg ttg gag ggt ctt gag aaa cta gaa     1700
```

```
            Ile Ala Asn Ile Asn Asp Asp Met Leu Glu Gly Leu Glu Lys Leu Glu
                    520                 525                 530 att ctc gat ttg cag cat aac aac tta gca cgg ctc tgg aaa cac gca          1748
Ile Leu Asp Leu Gln His Asn Asn Leu Ala Arg Leu Trp Lys His Ala
        535                 540                 545 aac cct ggt ggt ccc att tat ttc cta aag ggt ctg tct cac ctc cac          1796
Asn Pro Gly Gly Pro Ile Tyr Phe Leu Lys Gly Leu Ser His Leu His
550                 555                 560                 565 atc ctt aac ttg gag tcc aac ggc ttt gac gag atc cca gtt gag gtc          1844
Ile Leu Asn Leu Glu Ser Asn Gly Phe Asp Glu Ile Pro Val Glu Val
                570                 575                 580 ttc aag gat tta ttt gaa cta aag atc atc gat tta gga ttg aat aat          1892
Phe Lys Asp Leu Phe Glu Leu Lys Ile Ile Asp Leu Gly Leu Asn Asn
            585                 590                 595 tta aac aca ctt cca gca tct gtc ttt aat aat cag gtg tct cta aag          1940
Leu Asn Thr Leu Pro Ala Ser Val Phe Asn Asn Gln Val Ser Leu Lys
        600                 605                 610 tca ttg aac ctt cag aag aat ctc ata aca tcc gtt gag aag aag gtt          1988
Ser Leu Asn Leu Gln Lys Asn Leu Ile Thr Ser Val Glu Lys Lys Val
615                 620                 625 ttc ggg cca gct ttc agg aac ctg act gag tta gat atg cgc ttt aat          2036
Phe Gly Pro Ala Phe Arg Asn Leu Thr Glu Leu Asp Met Arg Phe Asn
                630                 635                 640                 645 ccc ttt gat tgc acg tgt gaa agt att gcc tgg ttt gtt aat tgg att          2084
Pro Phe Asp Cys Thr Cys Glu Ser Ile Ala Trp Phe Val Asn Trp Ile
            650                 655                 660 aac gag acc cat acc aac atc cct gag ctg tca agc cac tac ctt tgc          2132
Asn Glu Thr His Thr Asn Ile Pro Glu Leu Ser Ser His Tyr Leu Cys
        665                 670                 675 aac act cca cct cac tat cat ggg ttc cca gtg aga ctt ttt gat aca          2180
Asn Thr Pro Pro His Tyr His Gly Phe Pro Val Arg Leu Phe Asp Thr
680                 685                 690 tca tct tgc aaa gac agt gcc ccc ttt gaa ctc ttt ttc atg atc aat          2228
Ser Ser Cys Lys Asp Ser Ala Pro Phe Glu Leu Phe Phe Met Ile Asn
            695                 700                 705 acc agt atc ctg ttg att ttt atc ttt att gta ctt ctc atc cac ttt          2276
Thr Ser Ile Leu Leu Ile Phe Ile Phe Ile Val Leu Leu Ile His Phe
710                 715                 720                 725 gag ggc tgg agg ata tct ttt tat tgg aat gtt tca gta cat cga gtt          2324
Glu Gly Trp Arg Ile Ser Phe Tyr Trp Asn Val Ser Val His Arg Val
                730                 735                 740 ctt ggt ttc aaa gaa ata gac aga cag aca gaa cag ttt gaa tat gca          2372
Leu Gly Phe Lys Glu Ile Asp Arg Gln Thr Glu Gln Phe Glu Tyr Ala
            745                 750                 755 gca tat ata att cat gcc tat aaa gat aag gat tgg gtc tgg gaa cat          2420
Ala Tyr Ile Ile His Ala Tyr Lys Asp Lys Asp Trp Val Trp Glu His
        760                 765                 770 ttc tct tca atg gaa aag gaa gac caa tct ctc aaa ttt tgt ctg gaa          2468
Phe Ser Ser Met Glu Lys Glu Asp Gln Ser Leu Lys Phe Cys Leu Glu
775                 780                 785 gaa agg gac ttt gag gcg ggt gtt ttt gaa cta gaa gca att gtt aac          2516
Glu Arg Asp Phe Glu Ala Gly Val Phe Glu Leu Glu Ala Ile Val Asn
790                 795                 800                 805 agc atc aaa aga agc aga aaa att att ttt gtt ata aca cac cat cta          2564
Ser Ile Lys Arg Ser Arg Lys Ile Ile Phe Val Ile Thr His His Leu
                810                 815                 820 tta aaa gac cca tta tgc aaa aga ttc aag gta cat cat gca gtt caa          2612
Leu Lys Asp Pro Leu Cys Lys Arg Phe Lys Val His His Ala Val Gln
            825                 830                 835
```

-continued

```
caa gct att gaa caa aat ctg gat tcc att ata ttg gtt ttc ctt gag    2660
Gln Ala Ile Glu Gln Asn Leu Asp Ser Ile Ile Leu Val Phe Leu Glu
        840                 845                 850 gag att cca gat tat aaa ctg aac cat gca ctc tgt ttg cga aga gga    2708
Glu Ile Pro Asp Tyr Lys Leu Asn His Ala Leu Cys Leu Arg Arg Gly
855                 860                 865 atg ttt aaa tct cac tgc atc ttg aac tgg cca gtt cag aaa gaa cgg    2756
Met Phe Lys Ser His Cys Ile Leu Asn Trp Pro Val Gln Lys Glu Arg
870                 875                 880                 885 ata ggt gcc ttt cgt cat aaa ttg caa gta gca ctt gga tcc aaa aac    2804
Ile Gly Ala Phe Arg His Lys Leu Gln Val Ala Leu Gly Ser Lys Asn
                890                 895                 900 tct gta cat taa atttatttaa atattcaatt agcaaaggag aaactttctc        2856
Ser Val His aatttaaaaa gttctatggc aaatttaagt tttccataaa ggtgttataa tttgtttatt  2916
catatttgta aatgattata ttctatcaca attacatctc ttctaggaaa atgtgtctcc  2976
ttatttcagg cctattttg acaattgact taatttacc caaataaaaa catataagca   3036
cgtaaaaaaa aaaaaaaaaa a                                            3057

<210> SEQ ID NO 2
<211> LENGTH: 904
<212> TYPE: PRT
<213> ORGANISM: Homo sapiens

<400> SEQUENCE: 2

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240
```

-continued

```
Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655
```

```
Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
        690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 3
<211> LENGTH: 21
<212> TYPE: PRT
<213> ORGANISM: Artificial Sequence
<220> FEATURE:
<223> OTHER INFORMATION: Primer

<400> SEQUENCE: 3

Cys Thr Cys Ala Gly Ala Ala Gly Ala Thr Thr Ala Cys Cys Ala Gly
1               5                   10                  15

Cys Cys Gly Cys Cys
            20

<210> SEQ ID NO 4
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
```

-continued

```
<222> LOCATION: (1)..(22)
<223> OTHER INFORMATION: See US2003/0165479

<400> SEQUENCE: 4
ccattatgag acagatctaa tg                                              22
```

TREATMENT OF CANCER USING TLR3 AGONISTS

CROSS REFERENCE TO RELATED APPLICATIONS

This application is a continuation-in-part of PCT/IB2004/004093, filed on Nov. 19, 2004, which is incorporated herein by reference in its entirety, including all references, Figures, Tables and nucleic acid and polynucleotide sequences.

The present invention relates generally to the fields of genetics and medicine. More specifically, the present invention relates to improved methods of treating cancers using TLR3 agonists.

INTRODUCTION

Cancer is one of the leading causes of death in Europe and in the United States. There are more than 1.2 million cancer cases each year in the U.S. and cancer is expected to be the leading cause of the death by the year 2010. Lung and prostate cancer are the top cancer killers for men in the United States. Lung and breast cancer are the top cancer killers for women in the United States. A cure for cancer has yet to be found. Current treatment options, such as surgery, chemotherapy and radiation treatment, are oftentimes either ineffective or present serious side effects.

Currently, cancer therapy may involve surgery, chemotherapy, hormonal therapy and/or radiation treatment to eradicate neoplastic cells in a patient. Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue.

Despite the availability of a variety of chemotherapeutic agents, chemotherapy has many drawbacks. Almost all chemotherapeutic agents are toxic, and chemotherapy causes significant, and often dangerous, side effects, including severe nausea, bone marrow toxicity, inummosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

Double-stranded RNA molecules, such as poly A-polyU and poly I-poly U, are immunostimulating agents. Preclinical studies performed in 1970-1980's showed that the incubation of blood mononuclear cells with poly A-poly U induces interferon alpha secretion, and that the injection of poly A-poly U activates natural killer cells in vitro (EP281 380; EP 113 162).

It has recently been demonstrated that the double-stranded RNA receptor is Toll Like receptor 3 (TLR3) (Alexopoulou et al., 2001). This receptor has been described to be expressed in membranes of dendritic cells and of cells from colic mucosa. The binding of double-stranded RNA to this receptor activates dendritic cells and activates T lymphocytes. Consequently, the use of double-stranded RNA for treating cancer has been attempted. However, the response rate was not high and no therapeutic applications were developed.

Therefore, a method allowing to select responding patient would greatly enhance the therapeutic efficacy of double-stranded therapies.

SUMMARY OF THE INVENTION

The present invention demonstrates the existence of a correlation between the expression of a TLR3 in cells from a tumor sample in a subject and the ability of said subject to respond to treatment with a composition comprising a TLR3 agonist, preferably an antibody or other TLR3 binding protein, a phosphate containing small molecule, an organophospho-ester, a nucleotide, nucleotide-like, nucleotide analog, or nucleic acid molecule, or most preferably a double-stranded RNA. More specifically, the present invention shows, for the first time, that TLR3 is expressed in tumoral cell membranes and that the binding of a TLR3 agonist, in particular double-stranded RNA, on said tumoral cells through the TLR leads to tumoral cells lysis and tumor regression. In contrast, tumoral cells that do not express TLR are not sensitive to a TLR3 agonist treatment, in particular the double-stranded RNA treatment. The finding is particularly surprising and important for the management of cancer patients because an increase in survival is rarely if ever achieved in any known active regimen in metastatic breast cancer. The usual finding is an improvement in early end-points (response rate and/or time to progression, otherwise known as progression-free survival) but the improvement almost never translates into a significant increase in overall survival, as exhibited in patients treated in accordance with the present invention.

Furthermore, the finding that TLR3 agonist therapy can increase survival will permit therapeutic strategies that are expected to be efficacious and a suitable treatment for tumors, including particularly breast tumors, whether they involve auxiliary lymph nodes or not, that is beyond only breast cancers presenting auxiliary lymph node involvement. Likewise, the TLR3 agonists may find use in breast (and other) cancers that are metastatic, recurring and/or refractory.

Accordingly, in another aspect, the present invention provides a method of treating a human subject having a tumor comprising TLR3-expressing cells, which method comprises administering to said patient a therapeutically effective amount of at least one TLR3 agonist. In a preferred embodiment, said human patient has a solid tumor. In a preferred embodiment, said human patient has a breast cancer.

Therefore, the present invention concerns the use of a TLR3 agonist for the manufacture of a medicament for treating cancer in a subject, wherein said cancer in said subject comprises cancer cells expressing a TLR3 receptor. Preferably, the TLR agonist is a TLR3 agonist. More preferably, the TLR3 agonist is a double-stranded RNA molecule. Optionally, the cancer is a metastatic cancer. In a particular embodiment, the present invention concerns the use of a double-stranded polyA/polyU RNA molecule for the manufacture of a medicament for treating a cancer in a subject, wherein said cancer in said subject comprises cancer cells expressing a TLR3 receptor. Preferably the cancer is a solid tumor or a carcinoma, for example a breast cancer.

The present invention also concerns a method for assessing the response of a subject having cancer to a treatment using a TLR3 agonist, the method comprising determining whether cancer cells in said subject express a TLR receptor, the expression of a TLR3 receptor being indicative of a responder subject. More preferably, the TLR3 agonist is a double-stranded RNA molecule.

The present invention further concerns a method for selecting subjects having a cancer that respond to a treatment using a TLR3 agonist, the method comprising determining whether cancer cells in said subject express a TLR3 receptor, the expression of a TLR3 receptor being indicative of a responder subject. More preferably, the TLR3 agonist is a double-stranded RNA molecule.

In addition, the present invention concerns a method for treating a subject having a cancer, the method comprising determining whether cancer cells in said subject express a TLR3 receptor, the expression of a TLR3 receptor being indicative of a subject responding to a TLR3 agonist, and treating said subject whose cancer cells express a TLR3 receptor with a TLR3 agonist. More preferably, the TLR3 agonist is a double-stranded RNA molecule.

Moreover, the inventors have surprisingly found in the follow up study to the 300 patient clinical trials that patients having a solid tumor and treated with a TLR3 agonist in accordance with a repeat-dose and with an intravenous therapeutic regimen exhibited greater survival than other patients not treated with the TLR3 agonist.

Accordingly, in one aspect, the present invention provides a method of achieving enhanced or prolonged survival in human patients with cancer, which comprises administering to said patient a therapeutically effective amount of at least one TLR3 agonist. In a preferred embodiment, said at least one TLR3 agonist is intravenously administered. In a preferred embodiment, the cancer is a breast cancer. In a more particular embodiment, the cancer is a metastatic or recurrent breast cancer. In another preferred embodiment, the cancer is a node positive breast cancer.

Accordingly, in one aspect, the present invention provides a method of achieving enhanced survival in human patients with cancer or a method for treating a subject having a cancer, which comprises administering to said patient (a) at least a first dose therapeutically effective amount of at least one TLR3 agonist; and (b) at least a second dose of a therapeutically effective amount of at least one TLR3 agonist. In a preferred embodiment, said first and said second doses are administered at an interval of less than one month, less than three weeks, less than two weeks, or less than one week.

In a preferred embodiment of the methods and uses according to the present invention, the subject is a human subject.

It will be appreciated that the methods of treatment mentioned herein can be used as prophylactic treatment; in any of the embodiments herein, a prophylatically effective amount of the TLR3 agonist can be interchanged with a therapeutically effective amount of a TLR3 agonist.

In a preferred embodiment of the methods and uses according to the present invention, the cancer is a solid tumor or a carcinoma. Preferably, the solid tumor is selected from breast cancer, colon cancer, lung cancer, prostate cancer, renal cancer, metastatic or invasive malignant melanoma, brain tumor, ladder cancer and liver cancer. Carcinoma includes bladder, breast, colon, kidney, liver, lung, ovary, pancreas, stomach, cervix, thyroid or skin carcinoma, including squamous cell carcinoma. In a most preferred embodiment, the solid tumor is a breast cancer. However, the present invention also contemplates hematopoietic tumors such as leukemia, acute lymphocytic leukemia, acute lymphoblastic leukemia, B-cell lymphoma, T-cell lymphoma, Hodgkins lymphoma, non-Hodgkins lymphoma, hairy cell lymphoma, Burketts lymphoma, acute and chronic myelogenous leukemias and promyelocytic leukemia. The present invention is also relevant for the treatment of metastasis.

In a preferred embodiment, the expression of a TLR3 receptor in said cancer cell is determined using a TLR3-specific ligand. Preferably, the ligand is an antibody, or a fragment or derivative thereof.

In an alternative embodiment, the expression of a TLR3 receptor in said cancer cell is determined using a TLR3-specific primer or probe.

Preferably, the expression of a TLR3 receptor in said cancer cell is determined in vitro or ex vivo. However, the determination in vivo is also encompassed by the present invention.

In a preferred embodiment of the methods and uses according to the present invention, the double-stranded RNA molecule is a polyA/polyU molecule. In another preferred embodiment of the methods and uses according to the present invention, the double-stranded RNA molecule is a polyI/polyC molecule.

The present invention further concerns a kit for selecting subjects that respond to a treatment using a TLR3 agonist, more preferably a double-stranded RNA molecule, the kit comprising reagents for determining the expression of a TLR3 receptor in a cancer cell in a sample.

DESCRIPTION OF THE FIGURES

The file of this patent contains at least one drawing executed in color. Copies of this patent or patent application publication with color drawings will be provided by the Patent and Trademark Office upon request and payment of the necessary fee.

DETAILED DESCRIPTION OF THE INVENTION

Figure 1:
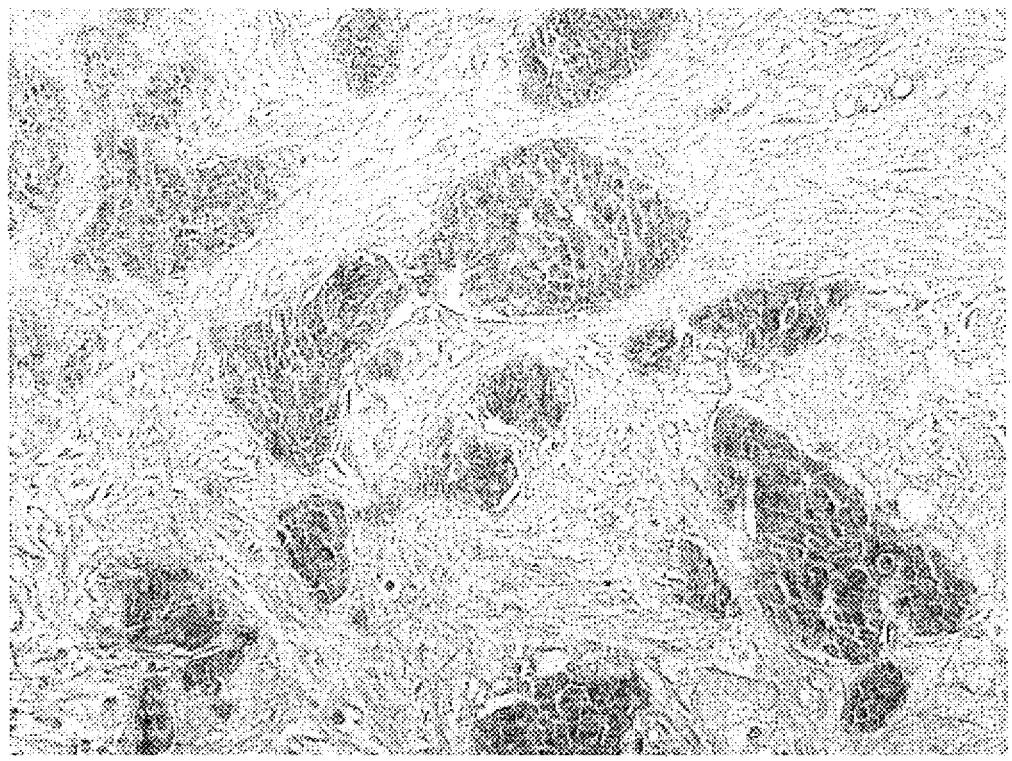
FIG. 1 illustrates the TLR3 expression by primary tumor. TLR3 is overexpressed by tumor cells in 10% of samples (n=18)

A marker-based approach to tumor identification and characterization promises improved diagnostic and prognostic reliability. Typically, the diagnosis of breast cancer and other types of cancer requires histopathological proof of the presence of the tumor. In addition to diagnosis, histopathological examinations also provide information about prognosis and selection of treatment regimens. Prognosis may also be established based upon clinical parameters such as tumor size, tumor grade, the age of the patient, and lymph node metastasis.

With the available and potent conventional drug regimens as well as the advent of novel therapy approaches targeting specific biological pathways, the determination of optimal treatment of a primary cancer is becoming increasingly complex. Moreover, the outcome of a treatment of a patient with cancer is often unpredictable. Only a portion of the patients respond to a certain type of treatment. The patients receiving a specific type of treatment are subjected to an unnecessary suffering since adverse reactions often are obtained from certain treatment used. Some treatments elicit more severe reaction from the patient than other treatments. Mostly, the effect of a treatment is not shown until 3-6 months after treatment. It would therefore be of great importance if patients with a high probability to respond could be identified before the onset of treatment. To date, no set of satisfactory predictors for prognosis or therapeutic response based on the clinical information alone has been identified for TLR agonist compounds in cancer therapy.

As further described herein, the studies disclosed herein present results from 300 patients with early breast cancer that had been included from 1972 to 1979 in a randomized trial comparing post-operative administration of TLR agonist polyAU with no treatment. When the TLR was investigated as a potential biomarker, it was observed that tumor biopsies positive for TLR demonstrated high long term survival rates, and presumably that this survival is in response to therapy with the TLR3 agonist. Patient biopsies were stained with a TLR3-specific mAb and correlation of TLR3 expression with polyAU efficacy was determined. 182 tumor samples (91%) were available from the 200 patients included in the randomized trial. TLR3 was strongly expressed by tumor cells in 18 patients (10%). TLR3 expression correlated with a significantly increased 20-year survival rate.

Accordingly, in one aspect, the present invention provides a method of determining whether a patient will respond to therapy with a TLR3 agonist. In one embodiment the present invention concerns a method for selecting or identifying a subject having a tumor that respond to a treatment using a TLR3 agonist, the method comprising determining whether tumor cells in said subject express a TLR3, the expression of a TLR3 receptor being indicative of a responder subject. In a preferred embodiment, TLR3 is determined using an immunohistochemical assay, as used in the Examples. Preferably TLR3 expression is determined using an antibody that specifically binds TLR3.

In another embodiment, the present invention provides a method for characterizing a cell or a tumor in a patient, the method comprising: obtaining or providing a biological sample from the patient, wherein said sample comprises a tumor cell or biological material derived therefrom, and determining whether said cell expresses a TLR3. In a preferred embodiment, the present invention provides a method for characterizing a cell or a tumor in a patient, the method comprising: obtaining or providing a tumor biopsy from the patient, and determining whether said biopsy comprises a cell expressing a TLR3 polypeptide.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can preferably be replaced by "consisting essentially of", more preferably by "consisting of".

Whenever within this whole specification "treatment of a proliferative disease" or "treatment of a tumor", or "treatment of cancer" or the like is mentioned with reference to a TLR3 agonist, there is meant:

a method of treatment (=for treating) of a proliferative disease, said method comprising the step of administering (for at least one treatment) a TLR3 agonist, (preferably in a pharmaceutically acceptable carrier material) to a warm-blooded animal, especially a human, in need of such treatment, in a dose that allows for the treatment of said disease (=a therapeutically effective amount), preferably in a dose (amount) as specified to be preferred hereinabove and herein below;

the use of a TLR3 agonist for the treatment of a proliferative disease; or a TLR3 agonist, for use in said treatment (especially in a human);

the use of a TLR3 agonist, for the manufacture of a pharmaceutical preparation for the treatment of a proliferative disease; and/or a pharmaceutical preparation comprising a dose of a TLR3 agonist that is appropriate for the treatment of a proliferative disease; or any combination of a), b), c) and d), in accordance with the subject matter allowable for patenting in a country where this application is filed;

a method of using a TLR3 agonist for the manufacture of a pharmaceutical preparation for the treatment of a proliferative disease, comprising admixing said TLR3 agonist with a pharmaceutically acceptable carrier. In cases where a tumor disease or a specific tumor (e.g. breast tumor, colon tumor, colon carcinoma or colon cancer; or prostate tumor, prostate carcinoma or prostate cancer) are mentioned instead of "proliferative disease", categories a) to e) are also encompassed, meaning that the respective tumor disease can be filled in under a) to e) above instead of "proliferative disease", in accordance with the patentable subject matter.

The terms "cancer" and "tumor" as used herein are defined as a new growth of cells or tissue comprising uncontrolled and progressive multiplication. In a specific embodiment, upon a natural course the cancer is fatal. In specific embodiments, a cancer is invasive, metastatic, and/or anaplastic (loss of differentiation and of orientation to one another and to their axial framework).

The term "breast cancer" as used herein is defined as cancer which originates in the breast. In a specific embodiment, the breast cancer spreads to other organs, such as lymph nodes. In a specific embodiment, the breast cancer is invasive and may be metastatic.

The term "invasive" as used herein refers to cells which have the ability to infiltrate surrounding tissue. In a specific embodiment, the infiltration results in destruction of the surrounding tissue. In another specific embodiment, the cells are cancer cells. In a preferred embodiment, the cells are breast cancer cells, and the cancer spreads out of a duct into surrounding breast epithelium. In a specific embodiment, "metastatic" breast cancer is within the scope of "invasive."

The term "metastatic" as used herein is defined as the transfer of cancer cells from one organ or part to another not directly connected with it. In a specific embodiment, breast cancer cells spread to another organ or body part, such as lymph nodes.

"Weekly" stands for "about once a week" (meaning that more than one treatment is made with an interval of about one week between treatments), the about here preferably meaning +/−1 day (that is, translating into "every 6 to 8 days"); most preferably, "weekly" stands for "once every 7 days".

The term "biopsy" as used herein is defined as removal of a tissue from an organ (e.g., breast) for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

As used herein, the term "adjunctive" is used interchangeably with "in combination" or "combinatorial". Such terms are also used where two or more therapeutic or prophylactic agents affect the treatment or prevention of the same disease. For the avoidance of doubt, two agents used "in combination" may be, but are not necessarily, co-administered.

As used herein, the term "in combination" refers to the use of more than one therapies (e.g., more than one prophylactic agent and/or therapeutic agent). The use of the term "in combination" does not restrict the order in which therapies (e.g., prophylactic or therapeutic agents) are administered to a subject with cancer. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with cancer.

By "co-administration" or "co-administering" we mean that the two agents are administered in temporal juxtaposition. The co-administration may be effected by the two agents being mixed into a single formulation, or by the two agents being administered separately but simultaneously, or separately and within a short time of each other. For example, in general the two agents are co-administered within the time range of 24-72-12 hours. In this case, the agents may be administered in either order, i.e. a TLR3 agonist may be administered first, or the inhibitor of a compensatory cytoprotective pathway may be administered first. In a preferred embodiment of the instant invention, the two agents are co-administered in a single formulation, or are co-administered simultaneously. Further, more than one cell cycle checkpoint abrogation agent or more than one inhibitor of a compensatory cytoprotective pathway may be administered together, and inhibitors of different compensatory cytoprotective pathways may be co-administered together.

As used herein, the terms "prevent", "preventing" and prevention refer the inhibition of the development or onset of cancer (particularly, a T-cell malignancy) or the prevention, recurrence, onset, or development of one or more symptoms of cancer, particularly a T-cell malignancy, in a subject resulting from the administration of therapy (e.g., a prophylactic or therapeutic agent) or a combination of therapies (e.g., a combination of prophylactic and/or therapeutic agents).

As used herein, the term "prophylactically effective amount" refers to that amount of the prophylactic agent sufficient to result in the prevention of the recurrence or onset of cancer or one or more symptoms thereof.

A used herein, a "protocol" includes dosing schedules and dosing regimens. The protocols herein are methods of use and include prophylactic and therapeutic protocols.

As used herein, a "prophylactic protocol" refers to a regimen for dosing and timing the administration of one or more prophylactic agents.

As used herein, the term "therapeutic protocol" refers to a regimen for dosing and timing the administration of one or more therapeutic agents.

As used herein, the phrase "side effects" encompasses unwanted and adverse effects of a therapy (e.g., prophylactic and/or therapeutic agent). Adverse effects are always unwanted, but unwanted effects are not necessarily adverse. An adverse effect from a prophylactic or therapeutic agent might be harmful or uncomfortable or risky.

As used herein, the term "small molecules" and analogous terms include, but are not limited to, organic or inorganic compounds (i.e., including heteroorganic and organometallic compounds) having a molecular weight less than 1,000 grams per mole. In a preferred embodiment, "small molecules" encompass organic or inorganic compounds having a molecular weight less than 750 grams per mole. In yet another specific embodiment, "small molecules" encompass organic or inorganic compounds having a molecular weight less than 500 grams per mole. Salts, esters, and other pharmaceutically acceptable forms of such compounds are also encompassed.

As used herein, the terms "subject" and "patient" are used interchangeably.

As used herein, the terms "subject" and "subjects" refer to an animal, preferably a mammal including, but not limited to, a non-primate (e.g., a cow, pig, horse, cat, dog, rat, and mouse) and a non-primate (e.g., a monkey such as a cynomolgous monkey and a human), and more preferably a human. In a specific embodiment, the subject is a human with cancer. In a preferred embodiment, the subject is a human with a solid tumor, for example a breast cancer.

As used herein, the term "synergistic" refers to a combination of therapies (e.g., prophylactic or therapeutic agents) which is more effective than the additive effects of any two or more single agents. For example, a synergistic effect of a combination of therapies (e.g., prophylactic or therapeutic agents) permits the use of lower dosages of one or more of the agents and/or less frequent administration of said therapies to a subject with cancer.

The ability to utilize lower dosages of therapies (e. g., prophylactic or therapeutic agents) and/or to administer said therapies less frequently reduces the toxicity associated with the administration of said therapies to a subject without reducing the efficacy of said therapies in the prevention or treatment of cancer. In addition, a synergistic effect can result in improved efficacy of therapies in the prevention or treatment of cancer. Finally, synergistic effect of a combination of therapies may avoid or reduce adverse or unwanted side effects associated with the use of any single therapy.

As used herein, the terms "therapeutic agent" and "therapeutic agents" refer to any agent (s) which can be used in the treatment, management, or amelioration of cancer or one or more symptoms thereof. In certain embodiments, the term "therapeutic agent" refers to a TLR3 agonist. In certain other embodiments, the term "therapeutic agent" does not refer to a TLR3 agonist. In yet other embodiments, the term "therapeutic agents" refers to a TLR3 agonist and a cancer therapy other than a TLR3 agonist. Preferably, a therapeutic agent is an agent which is known to be useful for, or has been or is currently being used for the treatment, management, or amelioration of cancer or one or more symptoms thereof. Therapeutic agents may be characterized as different agents based upon one or more effects the agents have in vivo and/or in vitro.

As used herein, the term "effective amount" refers to the amount of a therapy (e. g. a prophylactic or therapeutic agent) which is sufficient to reduce or ameliorate the severity, duration and/or progression of cancer or one or more symptoms thereof, ameliorate one or more symptoms of cancer, prevent the advancement of cancer, cause regression of cancer, prevent the recurrence, development, or onset of cancer or one or more symptoms thereof, or enhance or improve the prophylactic or therapeutic effect (s) of another therapy (e.g., prophylactic or therapeutic agent).

As used herein, the term "therapeutically effective amount" refers to that amount of a therapy (e.g., a therapeutic agent) which is sufficient to destroy, modify, control or remove primary, regional or metastatic cancer tissue, ameliorate cancer or one or more symptoms thereof, or prevent the advancement of cancer, cause regression of cancer, or enhance or improve the therapeutic effect (s) of another therapy (e.g., a therapeutic agent).

A therapeutically effective amount may refer to the amount of a therapy (e.g., a therapeutic agent) sufficient to delay or minimize the spread of cancer. A therapeutically effective amount may also refer to the amount of a therapy (e.g., a therapeutic agent) that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of cancer. Used in connection with an amount of a TLR3 agonist, the term can encompass an amount that improves overall therapy, reduces or avoids unwanted effects, or enhances the therapeutic efficacy of or synergizes with another therapy (e.g., a therapeutic agent).

As used herein, the terms "treat", "treatment" and "treating" refer to the reduction or amelioration of the progression, severity, and/or duration of cancer, particularly a solid tumor, for example a breast cancer, or one or more symptoms thereof that results from the administration of one or more therapies (e.g., one or more prophylactic and/or therapeutic agents).

As used herein, the terms "prevent", "preventing", and "prevention" refer to the prevention of the recurrence, onset, or development of cancer or one or more symptoms thereof in a subject, said prevention resulting from a therapy (e.g., the administration of a prophylactic or therapeutic agent), or a combination therapy (e.g., the administration of a combination of prophylactic or therapeutic agents).

As used herein, the terms "therapies" and "therapy" can refer to any protocol (s), method (s) and/or agent (s) that can be used in the prevention, treatment, management or amelioration of cancer or one or more symptoms thereof. In certain embodiments, the terms "therapy" and "therapies" refer to cancer chemotherapy, radiation therapy, hormonal therapy, biological therapy, and/or other therapies useful for the prevention, management, or treatment of cancer known to an oncologist skilled in the art.

As used herein, the terms "manage", "managing", and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents) to "manage" a disease so as to prevent the progression or worsening of the disease.

The term "TLR3 agonist" refers to an affinity agent (i.e., a molecule that binds a target molecule) capable of activating a TLR3 polypeptide to induce a full or partial receptor-mediated response. For example, an agonist of TLR3 induces TLR3-mediated signalling, either directly or indirectly. A TLR3 agonist, as used herein, may but is not required to bind a TLR3 polypeptide, and may or may not interact directly with the TLR3 polypeptide.

A "nucleotide agonist" or "nucleic acid agonist" refers to the situation where the affinity agent comprises or consists of nucleotides and/or nucleic acid(s). "Antibody agonist" refers to the situation where the affinity agent is an antibody.

The terms "polynucleotide" and "nucleic acid", used interchangeably herein, refer to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:23181 0 2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by nonnucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

As used herein, the term "host cell" includes a particular subject cell transfected with a nucleic acid molecule and the progeny or potential progeny of such a cell.

The percent identity between the two sequences is a function of the number of identical positions shared by the sequences (i.e., % identity number of identical overlapping positions/total number of positions×100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences used. The percent identity between two sequences can be determined using techniques similar to those described above, with or without allowing gaps. In calculating percent identity, typically only exact matches are counted.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95% or 98%) identical to each other typically remain hybridized to each other. Such stringent conditions are known to those skilled in the art and can be found in Current Protocols in Molecular Biology, John Wiley & Sons, N.Y. (1989). In one, non-limiting example stringent hybridization conditions are hybridization at 6× sodium chloride/sodium citrate (SSQ at about 45° C., followed by one or more washes in 0.1×SSC, 0.2% SDS at about 68° C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides. In a particular embodiment, typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

TLR3

"TLR3", "TLR3 polypeptide" and "TLR3 receptor", used interchangeably, are used herein to refer to Toll Like Receptor 3, a member of the Toll-like receptor (TLRs) family. Its amino acid sequence of is shown in SEQ ID NO: 2 (NCBI accession number NP_003256, the disclosure of which is incorporated herein by reference). As mentioned, it will be appreciated that any TLR3 polypeptide fragment or homologue can be used in accordance with the present methods. In one aspect, the TLR3 polypeptide may comprise an amino acid sequence of at least about 25, 30, 35, 40, 45, 50, 60, 70, 80, 100, 200, 300, 400, 500, 600, 700, 800, 900 or 904 amino acid residues in length, of which at least about 50-80%, preferably at least about 60-70%. more preferably at least about 65%, 75%, 80%, 85% or 90%. 95%, 98%, 99% or 99.5% of the amino acid residues are identical or similar amino acids to the sequence of the full-length native human TLR3 polypeptide (for example SEQ ID NO: 2 for human TLR3). Identity or similarity may be determined using any desired algorithm, including the algorithms and parameters for determining homology which are described herein.

Toll Like Receptor 3 is a member of the Toll-like receptor (TLR) family which plays a fundamental role in pathogen recognition and activation of innate immunity. TLRs are highly conserved from Drosophila to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This receptor is most abundantly expressed in placenta and pancreas, and is restricted to the dendritic subpopulation of the leukocytes. It recognizes dsRNA associated with viral infection, and induces the activation of NF-kappaB and the production of type I interferons. It may thus play a role in host defense against viruses. TLR3 mRNA sequence is described in NCBI accession number NM_003265, the sequence of which is shown in NO: 1. TLR3 is described in WO 98/50547 (the disclosure of which is incorporated herein by reference).

As used in the present application, the term "TLR3 gene" designates the Toll Like Receptor 3 gene, as well as variants, analogs and fragments thereof, including alleles thereof (e.g., germline mutations). Such variants include, for instance, naturally-occurring variants due to allelic variations between individuals (e.g., polymorphisms), alternative splicing forms, etc. Variants are preferably substantially homologous to NM_003265 sequence, i.e., exhibit a nucleotide sequence identity of at least about 65%, typically at least about 75%, preferably at least about 85%, more preferably at least about 95% with NM_003265 sequence. A particular example of a TLR3 gene comprises NM_003265 sequence. Variants and analogs of a TLR3 gene also include nucleic acid sequences, which hybridize to a sequence as defined above (or a complementary strand thereof) under stringent hybridization conditions.

A fragment of a TLR3 gene designates any portion of at least about 8 consecutive nucleotides of a sequence as disclosed above, preferably at least about 15, more preferably at least about 20 nucleotides, further preferably of at least 30 nucleotides. Fragments include all possible nucleotide lengths between 8 and 100 nucleotides, preferably between 15 and 100, more preferably between 20 and 100.

The term "gene" shall be construed to include any type of coding nucleic acid, including genomic DNA (gDNA), complementary DNA (cDNA), synthetic or semi-synthetic DNA, as well as any form of corresponding RNA. The term gene particularly includes recombinant nucleic acids encoding TLR3, i.e., any non naturally occurring nucleic acid molecule created artificially, e.g., by assembling, cutting, ligating or amplifying sequences. A TLR3 gene is typically double-stranded, although other forms may be contemplated, such as single-stranded. TLR3 genes may be obtained from various sources and according to various techniques known in the art, such as by screening DNA libraries or by amplification from various natural sources. Recombinant nucleic acids may be prepared by conventional techniques, including chemical synthesis, genetic engineering, enzymatic techniques, or a combination thereof.

A TLR3 polypeptide designates any protein or polypeptide encoded by a TLR3 gene as disclosed above. The term "polypeptide" refers to any molecule comprising a stretch of amino acids. This term includes molecules of various lengths, such as peptides and proteins. The polypeptide may be modified, such as by glycosylations and/or acetylations and/or chemical reaction or coupling, and may contain one or several non-natural or synthetic amino acids. A specific example of a TLR3 polypeptide comprises all or part of NP_003256 sequence.

TLR3-expressing Tumors Types

It has also been found that certain classes of patients with cancer treated in accordance with the procedure described using a TLR3 agonist exhibit greater survival than other patients. One class of patients in which enhanced survival was found were patients having tumors that express a TLR3 protein.

Determining whether tumor types express TLR3 can be carried out as described in the examples, e.g. by detecting the presence of one or more TLR3 polypeptides in a biological sample from a cancer patient, generally from a tumor biopsy. The inventors provide herein that several tumor types can express TLR3 proteins and that these types of tumors can be treated with a TLR3 agonist according to the invention.

In other specific embodiments, a diagnostic assay is performed on a tumor sample from a patient to determine whether the tumor sample comprises TLR3-expressing cells. Such assays are described herein; for example antibody-based immunohistochemistry assays can be used advantageously. Preferably a tumor biopsy is performed, yielding a biological sample. A determination that said biological sample comprises TLR3 expressing cells indicates that the patient can benefit from the TLR3 agonist administration. The patient is then treated with the TLR3 agonist.

Preferably, the step of determining whether cancer cells in said subject express a TLR3 receptor is performed on a tumoral sample derived from a patient. For example, the sample can be a biopsy of the patient's tumor, a cell or tissue culture, etc. Such sample can be obtained by conventional methods. In a particular embodiment, the sample is obtained by non-invasive methods and/or from tissue collections.

Therefore, in one embodiment of the methods and uses according to the present invention, the step of determining whether cancer cells in said subject express a TLR3 receptor comprises providing a tumoral sample from the patient and detecting the expression of a TLR3. The expression of a TLR3 may be detected at the nucleic acid level or at the polypeptide level.

Various techniques known in the art may be used to detect or quantify TLR3, including sequencing, hybridisation, amplification and/or binding to specific ligands (such as antibodies). Suitable methods include Southern blot (for DNAs), Northern blot (for RNAs), fluorescent in situ hybridization (FISH), gel migration, ELISA, radio-immunoassays (RIA) and immuno-enzymatic assays (IEMA).

Some of these approaches are particularly suited for assessing a polypeptide sequence or expression level, such as Northern blot, ELISA and RIA. These latter require the use of a ligand specific for the polypeptide, more preferably of a specific antibody.

Different types of ligands may be used, such as specific antibodies. In a specific embodiment, the sample is contacted with an antibody specific for a TLR3 polypeptide and the formation of an immune complex is determined. Various methods for detecting an immune complex can be used, such as ELISA, radioimmunoassays (RIA) and immuno-enzymatic assays (IEMA).

Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, poly-functional antibodies, etc. TLR3-specific antibodies suitable for use in the present invention are commercially available, such as (TLR3 monoclonal antibodies, Ref 12-9039 and 12-9039, eBioscience, USA; or polyclonal anti TLR3, Ref ab13555, abcam, UK; etc).

In a specific embodiment, the method comprises contacting a sample from the subject with (a support coated with) an antibody specific for TLR3 polypeptide, and determining the presence of an immune complex.

In an alternative embodiment, the expression of a TLR3 receptor in said cancer cell is determined using a TLR3-specific primer or probe. Such primer or probes are designed to specifically hybridise with a TLR3 gene, under suitable hybridisation conditions, thereby allowing detection of a gene or RNA coding for TLR3. A particular embodiment comprises contacting a tumor sample from the patient with a TLR3-specific primer or probe, and determining the existence of a hybrid or amplification product. The presence (or amount) of TLR3 mRNA in a sample can provide an indication as to the expression of said receptor. Such determination may be accomplished by various techniques known in the art, including through RT-PCR. To that purpose, total RNA is isolated from cancer cells using commercially available kits, such as the RNeasy Mini kit (Qiagen, Valencia, Calif.). DNase I-treated total RNA (3 μg) is reverse-transcribed by using random primers with RNaseH-free reverse transcriptase (Invitrogen, San Diego, Calif.). TLR3 can be amplified using specific primers described below. TLR3 (5'-CTCAGAAGATTACCAGC-CGCC-3' (SEQ ID NO: 3)/5'-CCATTATGAGACA-GATCTAATG-3' (SEQ ID NO: 4)) (see US2003/0165479, the disclosure of which is incorporated herein by reference).

Prior to determining expression of TLR3, the sample may be treated to improve availability of TLR3 nucleic acids or polypeptides. Such treatment may include, for instance, a lysis of the cells or tissue (e.g., mechanical, enzymatic or physical).

The invention also relates to a diagnostic kit comprising products and reagents for detecting in a tumoral sample from a subject the expression of a TLR3 gene or polypeptide. Said diagnostic kit according to the present invention comprises any primer, any pair of primers, any nucleic acid probe and/or any ligand, preferably antibody, described in the present invention. Said diagnostic kit according to the present invention can further comprise reagents and/or protocols for performing a hybridization, amplification or antigen-antibody immune reaction.

In addition to the discovery that breast cancer patients treated with TLR3 agonist demonstrate increased survival, it was found that a class of patients in which enhanced survival was found when treated in accordance with the procedure described using a TLR3 agonist were patients having metastatic or recurrent, or aggressive breast cancers. Another class of patients in which enhanced survival was found when treated in accordance with the procedure described using a TLR3 agonist were patients having lymph node positive breast cancers.

It is provided that cells from breast cancer samples express TLR3. However, it is also envisaged that samples from subjects having other tumor types will contain cells expressing TLR3, and that these subjects can be treated with TLR3 agonists; it will be appreciated that the skilled person may determine which tumors are suitable for treatment using available methods, including the methods described herein.

TLR3 Agonists

The TLR3 agonists according to the present invention can be selected from any suitable agent. For example, TLR3 agonists can be selected from a range of nucleic acid agonists; other agonists, whether nucleic acid based, proteinaceous or small molecules, can be tested using known assays.

Generally, any proteinaceous, nucleic acid or small molecule candidate TLR3 agonist can be identified using known assays. For example, assays for detecting TLR3 agonism of test compounds are described, for example, in PCT publication nos. WO 03/31573, WO 04/053057, WO 04/053452, and WO 04/094671, the disclosures of each of which are incorporated herein by reference.

Regardless of the particular assay employed, a compound can be identified as an agonist of TLR3 if performing the assay with a compound, which results in at least a threshold increase of some biological activity mediated by TLR3. Conversely, a compound may be identified as not acting as an agonist of TLR3 if, when used to perform an assay designed to detect biological activity mediated by TLR3, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR3 agonism of a compound in a particular assay. The precise threshold increase of TLR3-mediated biological activity for determining whether a particular compound is or is not an agonist of TLR3 in a given assay may vary according to factors known in the art including but not limited to the biological activity observed as the endpoint of the assay, the method used to measure or detect the endpoint of the assay, the signal-to-noise ratio of the assay, the precision of the assay. For example, regardless of the particular assay employed, a compound can generally be identified as an agonist of TLR3 if performing the assay with a compound results in at least a threshold increase of some biological activity mediated by TLR3.

An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR3 agonism of a compound in a particular assay, and whether the same assay is being used to determine the agonism of a compound for multiple TLRs.

The precise threshold increase of TLR3-mediated biological activity for determining whether a particular compound is or is not an agonist of TLR3 in a given assay may vary according to factors known in the art including but not limited to the biological activity observed as the endpoint of the assay, the method used to measure or detect the endpoint of the assay, the signal-to-noise ratio of the assay, the precision of the assay, and whether the same assay is being used to determine the agonism of a compound for multiple TLRs. Accordingly it is not practical to set forth generally the threshold increase of TLR3-mediated biological activity required to identify a compound as being an agonist or a non-agonist of TLR3 for all possible assays. Those of ordinary skill in the art, however, can readily determine the appropriate threshold with due consideration of such factors.

Assays employing HEK293 cells transfected with an expressible TLR3 structural gene may use a threshold of, for example, at least a three-fold increase in a TLR3-mediated biological activity (e.g., NF-KB activation) when the compound is provided at a concentration of, for example, from about 1 microM to about 10 microM for identifying a compound as an agonist of the TLR3 transfected into the cell. However, different thresholds and/or different concentration ranges may be suitable in certain circumstances. Also, different thresholds may be appropriate for different assays.

In certain embodiments, the TLR3 agonist can be a natural agonist of a TLR3 or a synthetic TLR3 agonist compound.

In preferred embodiments of the invention, a TLR3 agonist is used to treat a patient. TLR3 agonists are well known in the art and suitable TLR3 agonists are available. Further TLR3 agonists, or derivatives or analogs of known TLR3 agonists can be readily identified, made and/or assessed.

The most commonly used TLR3 agonist are nucleic acid based agonists. Thus in preferred aspects, a TLR3 agonist for use according to the present invention are nucleotide or nucleic acid based. Nucleotide or nucleic-acid based compounds can be assessed for their ability to act as an TLR3 agonist using readily available methods. The nucleic acid based TLR3 agonist can be single-stranded or double-stranded or a mixture thereof. The nucleic acid based TLR3 agonist can comprise deoxyribonucleotides, or ribonucleotides or a mixture thereof. The nucleotides can be natural or synthetic, and may be derivatives or analogs of natural nucleotides, such as for example in Kandimalla et al. ((2003) Nucl. Acid. Res. 31(9): 2393-2400).

The particular TLR3 agonist used in the clinical study, the analysis of which was at the origin of the observations on which the present invention is based was a double stranded RNA compound (dsRNA). The specific compound was polyadenylic-polyuridylic acid, i.e., poly(A): poly(U), polyAU or poly A:U. Double-stranded RNA which represents either genomic or life cycle intermediate material of many viruses activates cells through binding to the dsRNA-dependent protein kinase (PKR), a kinase that initiates a complex molecular anti-viral program (Gil, J., Alcami, J., and Esteban, M. 1999. Induction of apoptosis by double-stranded-RNA-dependent protein kinase (PKR) involves the alpha subunit of eukaryotic translation initiation factor 2 and NF-kappaB. Mol Cell Biol 19:4653-4663). dsRNA was however only recently suggested to act through TLR3 (Alexopoulou, L., Holt, A. C., Medzhitov, R., and Flavell, R. A. 2001. Recognition of double-stranded RNA and activation of NF-kappaB by Toll-like receptor 3. Nature 413:732-738). It was reported that dsRNA triggers the production of type 1 IFN, and dsRNA has been reported to have promise for certain clinical applications such as anti-viral therapies. A dsRNA compound referred to as Ampligen, for example, has been studied for its ability induce type 1 IFN production and as a consequence to treat viral infection.

Within the context of the present invention, the term "double-stranded RNA" molecule designates any therapeutically or prophylactically effective (synthetic) double-stranded RNA compound. Such compounds are typically active per se, i.e., they do not encode a polypeptide or do not require translation to be active. dsRNA TLR3 agonists can have any suitable length. Preferably, a dsRNA molecule TLR3 agonist has a length of at least about 10 base pairs (bp), 20 bp, 30 bp, 50 bp, 80 bp, 100 bp, 200 bp, 400 bp, 600 bp, 800 bp or 1000 bp. In one aspect the dsRNA molecule is a short dsRNA having a chain length of less than 30 bp, 50 bp, 80 bp, 100 bp or 200 bp. In another embodiment, the dsRNA molecule is a longer dsRNA, but having a chain length of less than 400 bp, 600 bp, 800 bp or 1000 bp. In another embodiment, the dsRNA molecule is a long dsRNA having a chain length of greater than 1000 bp. In one aspect, a dsRNA composition comprises a heterogenous mixture of dsRNA molecules, wherein a plurality of molecules have differing lengths. Preferably the dsRNA molecules have on average a length of at least about 10 bp, 20 bp, 30 bp, 50 bp, 80 bp, 100 bp, 200 bp, 400 bp, 600 bp, 800 bp or 1000 bp. In another embodiment, a dsRNA composition comprises a plurality dsRNA molecules where at least 20%, 50%, 80%, 90% or 98% of dsRNA molecules have a length of at least about 10 bp, 20 bp, 30 bp, 50 bp, 80 bp, 100 bp, 200 bp, 400 bp, 600 bp, 800 bp or 1000 bp. In a preferred embodiment dsRNA composition has a substantially homogenous mixture of dsRNA molecules, where substantially all the molecules do not differ in chain length by more than 30 bp, 50 bp, 80 bp, 100 bp or 200 bp. Average chain length of nucleic acid TLR3 agonists can be determined easily, for example, by gel permeation chromatography.

Previous studies of double-stranded RNA (dsRNA) assessing their ability to be effective interferon inducers suggested that dsRNA agents must possess the secondary structure of a double stranded helix. Other dsRNA agents which have also been shown to be suitable as TLR3 agonist include double-stranded polynucleotides which are not complementary or not perfectly complementary; these have been known as, so-called "mismatched" or "loop-out" structures and exist in naturally occurring RNAs such as transfer tRNAs, ribosomal RNAs and the viral RNA secondary structures. One commonly cited dsRNA compound, Ampligen, comprises a structure where a few parts of cytidine in the poly I:poly C structure are replaced with uridine (i.e. mismatched RNA); this compound has been reported to have physiological activity similar to that of the parent poly I:poly C. However it will be appreciated that TLR3 agonists of any type and configuration can be used in accordance with this invention.

Generally, the polynucleotides need to be resistant to nucleases in order to remain as macromolecules for a sufficient length of time; polynucleotides are less sensitive to nuclease attack when they are in a helical complex. However, certain analogs such as Ampligen™ appear to retain their TLR3 agonist activity.

In a particular embodiment, each strand of these dsRNAs can have a length comprised between about 5 and 50 bases, more preferably between 5 and 40, 35, 30, 25 or 20 bases. Each strand is preferably perfectly complementary to the other. Preferred examples of such dsRNAs are homopolyRNAs, i.e., dsRNAs in which each strand comprises essentially a repeat of the same base; or comprise a homopolyRNA region.

The base may be any naturally occurring base (e.g., polyA, polyU, polyC, polyG) or non-naturally occurring (e.g., chemically synthesized or modified) base (e.g., polyI). Polynucleotides typified by polyinosinic—polycytidylic acid, i.e., poly(I): poly(C) or poly I:C and polyadenylic-polyuridylic acid, i.e., poly(A): poly(U) or poly A:U, are well-known compounds in the art and have been known to induce interferon production by immune cells. Thus in preferred embodiments, the TLR3 agonist for use according to the invention is a double stranded nucleic acid selected from the group consisting of: polyinosinic acid and polycytidylic acid, polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue.

It will be appreciated that nucleic acid-based agonists of TLR3 can be designed using any suitable method. Preferably, the basic requirement of stability and resistance to nuclease attack and the preferences for chain length are taken into account, and that structural changes can be tested and assessed with reference to the a $rA_n:rU_n$ or $rI_n:rC_n$ complex for example. Measures can be taken to increase stability and resistance to nucleases, or to increase or optionally decrease interferon-inducing action.

Other examples of dsRNA include nucleic acids described in U.S. Pat. Nos. 5,298,614 and 6,780,429. U.S. Pat. No. 5,298,614 reports that when chain length of the double stranded nucleic acid derivatives is limited to certain ranges, the resulting substances exhibit desired physiological activity with markedly less toxicity, providing polynucleotides having a length of about 50 to 10,000 as calculated by base pair numbers. Also described are derivative wherein the purine or pyrimidine ring in the nucleic acid polymer is substituted with at least one SH group, or said derivative contains a disulphide bond, or both (preferred ratio of number of sulphur atoms to cytidylic acid present in the poly C are 1:6 to 39). U.S. Pat. No. 6,780,429 describes a particular type of dsRNA compounds that are "chain-shortened" having lengths of about 100 to 1,000 as calculated by base pair numbers, or preferably from 200 to 800, and more preferably from 300 to 600. The latter compounds are reported to contain low numbers of 2'-5' phosphodiester bonds by a method designed to avoid phosphate groups causing intramolecular rearrangement from 3' position to 2' position through a mechanism called pseudo rotation simultaneously that can occur during hydrolysis of poylnucleotides, resulting in a portion of 3'-5' phosphodiester bonds in the chain-shortened polynucleotide molecule being replaced by 2'-5' phosphodiester bonds. The disclosures of each of these references is incorporated herein by reference.

Other nucleic acid agonists that can be suitable for use as TLR3 agonists are provided in: Field et al.: Proc. Nat. Acad. Sci. U.S. 58, 1004, (1967); Field et al.: Proc. Nat. Acad. Sci. U.S. 58, 2102, (1967); Field et al.: Proc. Nat. Acad. Sci. U.S. 61, 340, (1968); Tytell et al.: Proc. Nat. Acad. Sci. U.S. 58, 1719, (1967); Field et al.: J. Gen. Physiol. 56, 905 (1970); De Clercq et al.: Methods in Enzymology, 78, 291 (1981). A number of synthetic nucleic acid derivatives have been described, including homopolymer-homopolymer complexes (Double Strand Nucleic Acid Polymer such as those in which poly I:C or poly A:U are a parent structure, where these homopolymer-homopolymer complexes contain: (1) base modifications, exemplified by Polyinosinic acid-poly (5-bromocytidylic acid), Polyinosinic acid-poly(2-thiocytidylic acid), Poly(7-deazainosinic acid)-polycytidylic acid, Poly(7-deazainosinic acid)-poly(5-bromocytidylic acid), and Polyinosinic acid-poly(5-thiouridylic acid); (2) Sugar Modifications, exemplified by Poly(2'-azidoinosinic acid)-polycytidylic acid; and (3) Phosphoric Acid Modifications, exemplified by Polyinosinic acid-poly(cytidyl-5'-thiophosphoric acid). Other synthetic nucleic acid derivatives that have been described include interchanged copolymers, exemplified by Poly(adenylic acid-uridylic acid); and homopolymer-copolymer complexes, exemplified by Polyinosinic acid-poly(cytidylic acid-uridylic acid) and Polyinosinic acid-poly(citydylic acid-4-thiouridylic acid). Other synthetic nucleic acid derivatives that have been described include complexes of synthetic nucleic acid with polycation, exemplified by Polyinosinic acid-polycytidylic acid-poly-L-lysinecarboxy-methylcellulose complex (called "Poly ICLC"). Yet another example of synthetic nucleic acid derivative is Polyinosinic acid-poly(1-vinylcytosine).

One example of a TLR3 agonist is Ampligen™ (Hemispherx, Inc., of Rockville, Md., U.S.A.), a dsRNA formed by complexes of polyriboinosinic and polyribocytidylic/uridylic acid, such as $rI_n:r(C_x,U$ or $G)_n$ where x has a value from 4 to 29, e.g., $rI_n:r(C_{12} U)_n$. Many mismatched dsRNA polymers which behave similarly to Ampligen have been studied; mismatched dsRNA based on poly I:C has included complexes of a polyinosinate and a polycytidylate containing a proportion of uracil bases or guanidine bases, e.g., from 1 in 5 to 1 in 30 such bases. The key therapeutic advantage of mismatched dsRNAs over other forms of natural and/or synthetic dsRNAs a reported reduction in toxicity over compounds such as those described in Lampson et al in U.S. Pat. No. 3,666,646.

Specific examples of double-stranded RNA according to the present invention further include Polyadenur (Ipsen) and Ampligen (Hemispherx). Polyadenur is a polyA/U RNA molecule, i.e., contains a polyA strand and a polyU strand. Polyadenur has been developed for the potential treatment of hepatitis B virus (HBV) infection. Ampligen is of a polyI/polyC compound (or a variant thereof comprising a polyI/polyC12U RNA molecule). Ampligen is disclosed for instance in EP 281 380 or EP 113 162. Ampligen has been proposed for the treatment of cancer, viral infections and immune disorders. It was developed primarily for the potential treatment of myalgic encephalomyelitis (ME, or chronic fatigue syndrome/chronic fatigue immune dysfunction syndrome, CFS/CFIDS).

A particular example of a dsRNA for use in the present invention is a dsRNA comprising a polyA/polyU region, wherein each strand of said dsRNA contains less than 25 bases.

Another particular example of a dsRNA for use in the present invention is a dsRNA comprising a polyI/polyC(U) region, wherein each strand of said dsRNA contains less than 25 bases.

Further dsRNAs have been disclosed in the literature or may be developed, which can be used within the present invention. More generally, any synthetic double-stranded homopolyRNA may be used in the context of this invention.

TLR3 agonist can also be any organic or inorganic substance, such as a lipid, peptide, polypeptide, small molecule, etc., in isolated or in mixture with other substances. The TLR3 agonist candidate may be selected from a combinatorial library of products, for instance. In a preferred embodiment, the TLR3 agonist is an antibody directed against TLR3 receptor and which is capable of activating a TLR3 receptor to induce a full or partial receptor-mediated response. The TLR3 agonist can also be an antibody fragment or derivative of an antibody directed against TLR3 receptor and which is capable of activating a TLR3 receptor to induce a full or partial receptor-mediated response.

Anti-TLR3 Antibodies

The present invention involves the production and use of antibodies, antibody fragments, or antibody derivatives that are suitable for use in humans and that target the TLR3 protein. The antibodies of this invention may be produced by any of a variety of techniques known in the art. Typically, they are produced by immunization of a non-human animal, preferably a mouse, with an immunogen comprising a TLR3 protein present on the surface of tumor cells. The receptor may comprise entire TLR3 expressing tumor cells, cell membranes, the full length sequence of the TLR3 protein, or a fragment or derivative thereof, typically an immunogenic fragment, i.e., a portion of the polypeptide comprising an epitope exposed on the surface of cells expressing the TLR3. Such fragments typically contain at least 7 consecutive amino acids of the mature polypeptide sequence, even more preferably at least 10 consecutive amino acids thereof. They are essentially derived from the extracellular domain of the TLR3 protein. In preferred embodiments, the TLR3 protein or peptide used to generate antibodies is a human TLR3 protein or peptide.

In a most preferred embodiment, the immunogen comprises a wild-type human TLR3 polypeptide in a lipid membrane, typically at the surface of a cell. In a specific embodiment, the immunogen comprises intact TLR3 expressing tumor cells, optionally treated or lysed.

In one embodiment, the antibodies are derived from one or more already-existing monoclonal antibodies that recognize the TLR3. Such antibodies can be directly or indirectly labeled (i.e., used with a labeled secondary antibody) for use as diagnostic antibodies for the herein-described typing step to determine the TLR3 status of patients. In addition, the antibodies can be made suitable for human administration (preferably chimeric, CDR-grafted, human or humanized antibodies) and, optionally, made toxic as described herein for use as cytotoxic antibodies in the present therapeutic methods.

The present diagnostic or therapeutic (e.g., cytotoxic) antibodies can be full length antibodies or antibody fragments or derivatives. Examples of antibody fragments include Fab, Fab', Fab'-SH, F(ab')$_2$, and Fv fragments; diabodies; single-chain Fv (scFv) molecules; single chain polypeptides containing only one light chain variable domain, or a fragment thereof that contains the three CDRs of the light chain variable domain, without an associated heavy chain moiety; single chain polypeptides containing only one heavy chain variable region, or a fragment thereof containing the three CDRs of the heavy chain variable region, without an associated light chain moiety; and multispecific antibodies formed from antibody fragments. Such fragments and derivatives and methods of preparing them are well known in the art. For example, pepsin can be used to digest an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into a Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology.

The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). For example, the repertoire may be any (recombinant) repertoire of antibodies or fragments thereof, optionally displayed by any suitable structure (e.g., phage, bacteria, synthetic complex, etc.).

The step of immunizing a non-human mammal with an antigen may be carried out in any manner well known in the art for (see, for example, E. Harlow and D. Lane, *Antibodies: A Laboratory Manual.*, Cold Spring Harbor Laboratory Press, Cold Spring Harbor, N.Y. (1988)). Generally, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In another embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, which are preferred for the purposes of the present invention, the next step is the isolation of cells, e.g., lymphocytes, splenocytes, or B cells, from the immunized non-human mammal and the subsequent fusion of those splenocytes, or B cells, or lymphocytes, with an immortalized cell in order to form an antibody-producing hybridoma. Accordingly, the term "preparing antibodies from an immunized animal," as used herein, includes obtaining B-cells/splenocytes/lymphocytes from an immunized animal and using those cells to produce a hybridoma that expresses antibodies, as well as obtaining antibodies directly from the serum of an immunized animal. The isolation of splenocytes, e.g., from a non-human mammal is well-known in the art and, e.g., involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the antibody-producing cells are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas can be grown on a feeder layer of macrophages. The macrophages are preferably from littermates of the non-human mammal used to isolate splenocytes and are typically primed with incomplete Freund's adjuvant or the like several days before plating the hybridomas. Fusion methods are described, e.g., in (Goding, "Monoclonal Antibodies: Principles and Practice," pp. 59-103 (Academic Press, 1986)), the disclosure of which is herein incorporated by reference.

The cells are allowed to grow in the selection media for sufficient time for colony formation and antibody production. This is usually between 7 and 14 days. The hybridoma colonies are then assayed for the production of antibodies that specifically recognize the desired substrate, e.g. a TLR3 protein. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically recloned and re-assayed to ensure that only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

In preferred embodiments, the DNA encoding an antibody that binds a determinant present on TLR3 is isolated from the hybridoma, placed in an appropriate expression vector for transfection into an appropriate host. The host is then used for the recombinant production of the antibody, variants thereof, active fragments thereof, or humanized or chimeric antibodies comprising the antigen recognition portion of the antibody.

DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al. (1993) Curr. Op. Immunol. 5:256; and Pluckthun (1992) Immunol. Revs. 130:151. Antibodies may also be produced by selection of combinatorial libraries of immunoglobulins, as disclosed for instance in Ward et al. (1989) Nature 341:544.

Various anti-TLR3 antibodies are commercially available. Examples include but are not limited to: Clone 40C1285, Imgenex Corp, Biocarta US, San Diego, Calif.; Clone TLR3.7, Catalog no. HM2096, HyCuit biotechnology B.V., The Netherlands; and Catalog no. 12-9039, Ebioscience Inc., San Diego, Calif.

Cancer and Therapeutic Methods

The present invention encompasses treatment protocols that provide better prophylactic or therapeutic profiles than current single agent therapies or combination therapies for cancer. In particular, the invention encompasses the use of a TLR3 agonist for the prevention, management, treatment or amelioration of cancer or one or more symptoms thereof.

Examples of cancers that can be prevented, managed, treated or ameliorated in accordance with the methods invention include, but are not limited to, solid tumors, and particularly cancers such as cancer of the head, neck, eye, mouth, throat, esophagus, chest, bone, lung, colon, rectum, stomach, prostate, breast, ovaries, kidney, liver, pancreas, and brain.

The invention provides methods for preventing, managing, treating or ameliorating cancer that has the potential to metastasize or has metastasized to an organ or tissue (e.g., bone) or one or more symptoms thereof, said methods comprising administering to a subject in need thereof one or more doses of a prophylactically or therapeutically amount of a TLR3 agonist. Preferably, the TLR3 agonist is a dsRNA compound. Preferably, the TLR3 agonist is administered more than once. Preferably, the TLR3 agonist is administered more than once. Optionally, the TLR3 agonist is administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The present invention provides methods for preventing, managing, treating or ameliorating cancer or one or more symptoms thereof, said methods comprising administering to a subject in need thereof a dosage of a prophylactically or therapeutically effective amount of a TLR3 agonist in combination with the administration of a dosage of a prophylactically or therapeutically effective amount of one or more other agents useful for cancer therapy. Preferably, the agonist is a dsRNA compound. Preferably, the TLR3 agonist is administered more than once. Optionally, the TLR3 agonist is administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The invention provides methods for preventing, managing, treating or ameliorating cancer that has is refractory to one or more therapeutic agents or therapies, said methods comprising administering to a subject in need thereof one or more doses of a prophylactically or therapeutically amount of a TLR3 agonist. Preferably, the TLR3 agonist is a dsRNA compound. Preferably, the doses are administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The present invention provides methods for preventing, treating, managing or ameliorating cancer or one or more symptoms thereof, said methods comprising administering to a subject in need thereof a TLR3 agonist alone or in combination with one or more other therapies (e.g., one or more other prophylactic or therapeutic agents) useful in the prevention, treatment, management or amelioration of cancer or one or more symptoms thereof. Preferably, the TLR3 agonist is a dsRNA compound.

In one embodiment, a TLR3 agonist (preferably, a dsRNA) is administered to a subject using a dosing regimen that maintains the plasma concentration of the agonist at a desirable level. In a specific embodiment, the plasma concentration of the dsRNA is maintained at 10 µg/ml, 15 µg/ml, 20 µg/ml, 25 µg/ml, 30 µg/ml, 35 µg/ml, 40 µg/ml, 45 µg/ml or 50 µg/ml. The plasma concentration that is desirable in a subject will vary depending on several factors including, but not limited to, the nature of the cancer, the severity of the cancer, and the circulation half-life (stability) and binding affinity of the TLR3 agonist.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight.

Preferably, a therapeutically effective amount of a TLR3 agonist (optionally in combination with another therapeutic agent or therapeutic protocol) reduces the size of a tumor or the spread of a tumor in a subject by at least 5%, preferably at least 10%, at least 15%, at least 20%, at least 25%, at least 30%, at least 35%, at least 40%, at least 45%, at least 50%, ate least 55%, at least 60%. at least 65%, at least 70%, at least 75%, at least 80%, at least 85%, at least 90%, at least 95% or at least 99% relative to a control such as PBS.

As used herein, the terms "non-responsive" and "refractory" describe patients treated with a currently available cancer therapy (e.g., chemotherapy, radiation therapy, surgery, hormonal therapy and/or biological therapy/immunotherapy), which is not clinically adequate to treat or relieve one or more symptoms associated with cancer. Typically, such patients suffer from severe, persistently active disease and. require additional therapy to ameliorate the symptoms associated with their cancer. The phrase can also describe patients who respond to therapy yet suffer from side effects, relapse, develop resistance, etc.

In various embodiments, "non-responsive/refractory" means that at least some significant portion of the cancer cells are not killed or their cell division arrested. The determination of whether the cancer cells are "non-responsive/refractory" can be made either in vivo or in vitro by any method known in the art for assaying the effectiveness of treatment on cancer cells, using the art-accepted meanings of "refractory" in such a context. In various embodiments, a cancer is "non-responsive/refractory" when the number of cancer cells has not been significantly reduced, or has increased.

Types of Cancers

In various embodiments, the present invention provides methods for determining treatment regimens for cancer subjects. The methods of the invention can be used to determine treatment regimens of any cancer, or tumor, for example, but not limited to, malignancies and related disorders include but are not limited to the following.

Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myclomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordonia, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glionia, astrocytoma, brain stem glioma, ependymoma, oligodendroglioma, nonglial tumor, acoustic neurinoma, craniopharyngioma, medulloblastoma, meningionia, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, and sarcoma; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, genn cell tumor, and stromal. tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fulminating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidemoid carcinoma), adenocarcinoma, large-cell carcinoma and small-cell lung cancer; testicular cancers such as but not limited to germinal tumor, seminoma, anaplastic, classic (typical), spermatocytic, nonserninoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocareinoma, mucoepidermoid carcinoma, and adenoidcystic carcinoma; pharynx cancers such as but not limited to squamous cell cancer, and cutaneous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilins' tumor; bladder cancers such as but not limited to transitional cell carcinoma, squamous cell cancer, adenocarcinoma, carcinosarcoma. In addition, cancers include inyxosarcoma, osteogenic sarcoma, endotheliosarcoma, lyinphangioendotheliosarcoma, mesothelioma, synovionia, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the methods of the invention are also useful in the treatment of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcilioma, neuroblastoma and glioma; tumors of the central and peripheral nervous system, including astrocytoma, neuroblastoma, glioma, and schwannomas; tumors of mesenchymal origin, including fibrosafconia, rhabdomyosearama, and osteosarcoma; and other tumors, including melanoma, xenoderma pegmentosum, keratoactanthoma, seminoma, thyroid follicular cancer and teratocarcinoma. In specific embodiments, malignancy or dysproliferative changes (such as metaplasias and dysplasias), or hyperproliferative disorders, are treated in the ovary, bladder, breast, colon, lung, skin, pancreas, or uterus. In other specific embodiments, sarcoma, melanoma, or leukemia is treated.

In preferred embodiments, the methods of the invention are used for TLR3 positive solid tumors. Example of tumors include breast, colon, ovarian, lung, brain and prostate cancers and melanoma. In a preferred embodiment, the methods of the invention are directed at treating breast cancer.

Breast Cancer

Types of Breast Cancer. Most breast cancer develops in glandular tissue and is classified as adenocarcinoma. The earliest form of the disease, ductal carcinoma in situ (DCIS), develops solely in the milk ducts. The most common type of breast cancer, invasive ductal carcinoma (IDC), develops from DCIS, spreads through the duct walls, and invades the breast tissue.

The term "premalignant lesion" as used herein is defined as a collection of cells in a breast with histopathological characteristics which suggest at least one of the cells has an increased risk of becoming breast cancer. A skilled artisan recognizes that the most important premalignant lesions recognized today include unfolded lobules (UL; other names: blunt duct adenosis, columnar alteration of lobules), usual ductal hyperplasia (UDH; other names: proliferative disease without atypia, epitheliosis, papillomatosis, benign proliferative disease), atypical ductal hyperplasia (ADH), atypical lobular hyperplasia (ALH), ductal carcinoma in situ (DCIS), and lobular carcinoma in situ (LCIS). Other lesions which may have premalignant potential include intraductal papillomas, sclerosisng adenosis, and fibroadenomas (especially atypical fibroadenomas). In a specific embodiment, the collection of cells is a lump, tumor, mass, bump, bulge, swelling, and the like. Other terms in the art which are interchangeable with "premalignant lesion" include premalignant hyperplasia, premalignant neoplasia, and the like.

Invasive lobular carcinoma originates in the milk glands and accounts for 10-15% of invasive breast cancers. Less common types of breast cancer include the following:

Inflammatory (breast tissue is warm and appears red; tends to spread quickly)

Medullary carcinoma (originates in central breast tissue)

Mucinous carcinoma (invasive; usually occurs in post-menopausal women)

Paget's disease of the nipple (originates in the milk ducts and spreads to the skin of the nipples or areola)

Phyllodes tumor (tumor with a leaf-like appearance that extends into the ducts; rarely metastasizes)

Tubular carcinoma (small tumor that is often undetectable by palpation)

Rarely, sarcomas (cancer of the connective tissue) and lymphomas (cancer of the lymph tissue) develop in the breasts.

Staging: The stage of a cancer is determined by the size and location in the body of the primary tumor, and whether it has spread to other areas of the body.

Staging involves using the letters T, N, and M to assess tumors:

size of the primary tumor (T);

degree to which regional lymph nodes (N) are involved. Lymph nodes are small organs located along the channels of the body's lymphatic system which store special cells that fight infection and other diseases); and absence or presence of distant metastases (M)—cancer that has spread from the original (primary) tumor to distant organs or distant lymph nodes.

Each of these categories is further classified with a number. Thus a T1-N1-M0 cancer would describe a T1 tumor, N1 lymph node involvement, and no metastases.

Once the T, N, and M components are determined, a "stage" of I, II, III or IV is assigned:

Stage I cancers are small, localized and usually curable.

Stage II and III cancers typically are locally advanced and/or have spread to local lymph nodes.

Stage IV cancers usually are metastatic (have spread to distant parts of the body) and generally are considered inoperable.

Details of this staging system are further provided in: The International Union against Cancer details the TNM staging system (Tumour/Nodes/Metastasis), (UICC—TNM Classification of malignant tumours. Edited by L. H. Sobin and C. H. Wittekind. 5th Edition. New York: Wiley-Liss; 1997)

The term "sample from a breast" as used herein is defined as a specimen from any part or tissue of a breast. A skilled artisan recognizes that the sample may be obtained by any method, such as biopsy. In another specific embodiment, the sample is from hyperplastic or malignant breast epithelium. In a specific embodiment, the sample is from the epithelium. In another specific embodiment, the sample is from a premalignant lesion.

In specific embodiments, a patient with breast cancer is administered a prophylactically or therapeutically effective amount of a TLR3 agonist. The patient may or may not have lymph node involvement, may or may not have metastates to distant organs or distant lymph nodes, may or may not have a recurrent cancer, or a cancer that is refractory or non-refractory. The cancer may be a stage I, II, III or IV cancer, most preferably a stage II or III cancer. The cancer may be a T1, T2 or T3 cancer. Optionally, the cancer is a T1-3N0-3M0 cancer. Optionally, the patient has received radiation therapy following surgery to remove breast cancer tissue. In another aspect, the patient has not received radiation therapy following surgery to remove breast cancer tissue.

Generally, although the therapeutic methods are not limited thereto, patients will have received surgery to remove breast cancer tissue. The TLR3 agonist may also be used a prophylactic agent before surgery, or more preferably is used in combination with surgery. The TLR3 agonist can advantageously be used soon or immediately after surgery (e.g beginning of TLR3 agonist treatment less than 8, 6, 4, 3, 2, 1 week following surgery), without possible adverse effects on TLR3 agonist efficacy related to immunosuppression that could be expected with immunomodulatory compounds.

In other specific embodiments, a diagostic assay is performed on a sample from a breast to determine whether a patient's tumor comprises TLR3-expression cells. Such assays are described herein; for example antibody-based immunohistochemistry assays can be used advantageously. Preferably a tumor biopsy is performed, yielding a biological sample. A determination that said biological sample comprises TLR3 expressing cells indicates that the patient can benefit from the TLR3 agonist administration. The patient is then treated with the TLR3 agonist.

In other specific embodiments, patients with breast cancer are administered a prophylactically or therapeutically effective amount of a TLR3 agonist in combination with a prophylactically or therapeutically effective amount of one or more other therapies useful for breast cancer treatment or management including, but not limited to: doxorubicin, epirubicin, the combination of doxorubicin and cyclophosphamide (AC), the combination of cyclophosphamide, doxorubicin and 5-fluorouracil(CAF), the combination of cyclophosphamide, epirubicin and 5-fluorouracil (CEF), Herceptin™), tamoxifen, or the combination of tamoxifen and cytotoxic chemotherapy. In certain embodiments, patients with metastatic breast cancer are administered a prophylactically or therapeutically effective amount of a TLR3 agonist in combination with the administration of a prophylactically or therapeutically effective amount of taxanes such as docetaxel and paclitaxel. In other embodiments, a patients with node-positive, localized breast cancer are administered a prophylactically or therapeutically effective amount of a TLR3 agonist in combination with the administration of a prophylactically or therapeutically effective amount of taxanes plus standard doxorubicin and cyclophosphamide for adjuvant treatment of node-positive, localized breast cancer.

Treatment of Colon Cancer

In specific embodiments, a patient with colon cancer is administered a prophylactically or therapeutically effective amount of a TLR3 agonist. The patient may or may not have metastates to distant organs or distant lymph nodes, may or may not have a recurrent cancer, or a cancer that is refractory or non-refractory. Optionally, the patient has received radiation therapy following surgery to remove cancerous tissue. In another aspect, the patient has not received radiation therapy following surgery to remove cancerous tissue.

Generally, although the therapeutic methods are not limited thereto, patients will have received surgery to remove cancer tissue. The TLR3 agonist may also be used a prophylactic agent before surgery, or more preferably is used in combination with surgery. The TLR3 agonist can advantageously be used soon or immediately after surgery (e.g beginning of TLR3 agonist treatment less than 8, 6, 4, 3, 2, 1 week following surgery), without possible adverse effects on TLR3 agonist efficacy related to immunosuppression.

In specific embodiments, patients with colon cancer are administered a prophylactically or therapeutically effective amount of a TLR3 agonist in combination with the administration of a prophylactically or therapeutically effective amount of one or more other therapies useful for colon cancer treatment or management including but not limited to: the combination of 5-FU and leucovorin, the combination of 5FU and levamisole, irinotecan (CPT-11) or the combination of irinotecan, 5-FU and leucovorin (IFL) or oxaliplatin.

Treatment of Prostate Cancer

In specific embodiments, patients with prostate cancer are administered a prophylactically or therapeutically effective amount of a TLR3 agonist in combination with the administration of a prophylactically or therapeutically effective amount of one or more other therapies useful for prostate cancer treatment or management including but not limited to: external-beam radiation therapy, interstitial implantation of radioisotopes (i.e., palladium, and Iridium), leuprolide or other LHR agonists, nonsteroidal antiandrogens (flutamide, nilutamide, and bicalutamide), steroidal antiandrogens (cyproterone acetate), the combination of leuprolide and flutainide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxcl, paclitaxel, estramustine/docetaxel, estramustine/etoposide, estramustine/vinblastine, and estramustine/paclitaxel.

Treatment of Melanoma

In specific embodiments, patients with melanoma are administered a prophylactically or therapeutically effective amount of a TLR3 agonist in combination with the administration of a prophylactically or therapeutically effective amount of one or more other therapies useful for melanoma cancer treatment or management including but not limited to: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2).

Treatment of Ovarian Cancer

In specific embodiments, patients with ovarian cancer are administered a prophylactically or therapeutically effective amount of a TLR3 agonist in combination with a prophylactically or therapeutically effective amount of one or more other therapies useful for ovarian cancer treatment or management including, but not limited to: intraperitoneal radiation therapy, total abdominal and pelvic radiation therapy, cisplatin, oxaliplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-fluorouracil (5FU) and leucovorin, etoposide, liposomal doxorubicin, gerucitabine or topotecan. In a particular embodiment, patients with ovarian cancer that is platinum-refractory are administered a prophylactically or therapeutically effective amount of a TLR3 agonist in combination with the administration of a prophylactically or therapeutically effective amount of Taxol. The invention encompasses the treatment of patients with refractory ovarian cancer including administration of—ifosfamide in patients with disease that is platinum-refractory, hexamethylmelamine (HAM) as salvage chemotherapy after failure of cisplatin-based combination regimens, and tamoxifen in patients with detectable levels of cytoplasmic estrogen receptor on their tumors.

Treatment of Lung Cancers

In specific embodiments, patients with small lung cell cancer are administered a prophylactically or therapeutically effective amount of a TLR3 agonist in combination with the administration of a prophylactically or therapeutically effective amount of one or more other therapies useful for lung cancer treatment or management including but not limited to: thoracic radiation therapy, cisplatin, vincristine, doxorubicin, and etoposide, alone or in combination, the combination of cyclophosphamide, doxorubicin, vincristine/etoposide, and cisplatin (CAV/EP), local palliation with endobronchial laser therapy, endobronchial stents, and/or brachytherapy.

In other specific embodiments, patients with non-small lung cell cancer are administered a prophylactically or therapeutically effective amount of a TLR3 agonist in combination with the administration of a prophylactically or therapeutically effective amount of one or more other therapies useful for lung cancer treatment or management including but not limited to: palliative radiation therapy, the combination of cisplatin, vinblastine and mitomycin, the combination of cisplatin and vinorelbine,pa. clitaxel, docetaxel or gemcitabine, the combination of carboplatin and paclitaxel, interstitial radiation therapy for endobronchial lesions or stereotactic radiosurgery Combination with Chemotherapy, Preferred Examples An adjunct therapy contemplated in the present invention is chemotherapy. Adjunct chemotherapies may include, for example, cisplatin (CDDP), carboplatin, oxaliplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitablen, navelbine, famesyl-protein transferase inhibitors, transplatinum, 5-fluorouracil, vincristin, vinblastin and methotrexate, or any analog or derivative variant of the foregoing.

Taxol/Paclitaxel. Paclitaxel, also known as taxol is a diterpene alkaloid thus it possesses a taxane skeleton in its structure. Paclitaxel is extracted from the bark of the Pacific yew (*Taxus brevifolia*) as a natural compound having anticancer activity (Fuchs and Johnson, 1978). Paclitaxel works against cancer by interfering with mitosis. Paclitaxel is a taxoid drug, widely used as an effective treatment of primary and metastatic cancers.

Paclitaxel (Taxol) is widely used in the treatment of breast, ovarian, and other solid tumors. Randomized clinical trials have shown a survival advantage among patients with primary breast cancer who received paclitaxel in addition to anthracycline-containing adjuvant chemotherapy (Eifel et al., 2001). Furthermore, paclitaxel is effective for both metastatic breast cancer (Holmes et al., 1991; Nabholtz et al., 1996; Bishop et al., 1999) and advanced ovarian cancer (McGuire et al., 1996; Piccart et al., 2000). The antitumor activity of paclitaxel is unique because it promotes microtubule assembly and stabilizes the microtubules, thus preventing mitosis (Huizing et al., 1995). Paclitaxel does this by reversibly and specifically binding to the B subunit of tubulin, forming microtubule polymers thereby stabilizing them against depolymerization and thus leading to growth arrest in the G2/M phase of the cell cycle (Gotaskie and Andreassi, 1994). This makes taxol unique in comparison to vincristine and vinblastine which cause microtubule disassembly (Gatzenicier et al., 1995). Additionally, recent evidence indicates that the microtubule system is essential to the release of various cytokines and modulation of cytokine release may play a major role in the drug's antitumor activity (Smith et al., 1995).

However, some patients are resistant to paclitaxel therapy, and the characteristics of patients who will benefit from the drug have not been well defined. Identification of molecular characteristics predictive of paclitaxel sensitivity or resistance could aid in selecting patients to receive this therapy. Thus, in particular embodiments, the present invention relates to paclitaxel sensitivity in a patient having cancer. Previous reports have demonstrated that paclitaxel resistance is due to a variety of mechanisms such as up-regulation of anti-apoptotic Bcl-2 family members, such as Bcl-2 and BCl-XL (Tang et al., 1994); up-regulation of membrane transporters (e.g., mdr-1), resulting in an increased drug efflux—(Huang et al., 1997); mutations in beta-tubulin resulting in abolishment of paclitaxel binding (Giannakakou et al., 1997); and up-regulation of ErbB2 (HER2) through inhibition of cyclin-dependent kinase-1 (Cdkl), resulting in delayed mitosis (Yu et al., 1998).

Due to the antimitotic activity of paclitaxel it is a useful cytotoxic drug in treating several classic refractory tumors. Paclitaxel has primarily been use to treat breast cancer and ovarian cancer. It may also be used in treating head and neck cancer, Kaposi's sarcoma and lung cancer, small cell and non-small cell lung cancer. It may also slow the course of melanoma. Response rates to taxol treatment varies among cancers. Advanced drug refractory ovarian cancer is reported to respond at a 19-36% rate, previously treated metastatic breast cancer at 27-62%, and various lung cancers at 21-37%. Taxol has also been shown to produce complete tumor remission in some cases (Guchelaar et al., 1994).

Paclitaxel is given intravenously since it irritates skin and mucous membranes on contact. It is typically administered intravenously by a 3 to 24 hour infusion three times per week (Guchelaar et al., 1994).

Doxorubicin. Doxorubicin hydrochloride, 5,12-Naphthacenedione, (8s-ds)-10-[(3-amino-2,3,6trideoxy-a-L-Iyxo-hexopyranosyl)oxy]-7,8,9,10-tetrahydro-6,8,11-trihydroxy-g-(hydroxyacetyl)1-methoxy-hydrochloride (hydroxydaunorubicin hydrochloride, Adriamycin) is used in a wide antineoplastic spectrum. It binds to DNA and inhibits nucleic acid synthesis and mitosis, and promotes chromosomal aberrations.

Administered alone, it is the drug of first choice for the treatment of thyroid adenoma and primary hepatocellular carcinoma. It is a component of first-choice in combination with other agents for the treatment of ovarian tumors, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Since doxorubicin is poorly absorbed it is administered intravenously. The pharmacokinetics of this chemotherapeutic agent are multicompartmental. Distribution phases have half-lives of 12 minutes and 3.3 hrs. The elimination half-life is about 30 hrs. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, for an adult, administered intravenously, are 60 to 75 mg/m$^2$ at 21-day intervals, or 25 to 30 mg/m$^2$ on each of 2 or 3 successive days repeated at 3- or 4-wk intervals, or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m2 in persons having received mediastinal irradiation. Alternatively, 30 mg/m$^2$ on each of 3 consecutive days, repeated every 4 wk may be administered. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 nig/m$^2$, 300mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the present invention.

Combination with Radiotherapy

Radiotherapy, also called radiation therapy, involves the use of ionizing radiation to treat cancers and other diseases. Ionizing radiation deposits energy that injurs or destroys cells in the area being treated (the "target tissue") by damaging their genetic material, and thereby inhibiting cell proliferation. Ionizing radiation induces the formation of hydroxyl radicals, placing the cells under oxidative stress. These radicals damage DNA, which causes cytotoxicity.

Radiotherapeutic agents that cause DNA damage are well known in the art and have been extensively used. Radiotherapeutic agents, through the production of oxygen-related free radicals and DNA damage, may lead to cell death or apoptosis. These agents may include, but are not limited to, 7-rays, X-rays, and/or the directed delivery of radioisotopes to tumor cells (known as internal radiotherapy). Internal radiotherapy may further include but is not limited to, brachytherapy, interstitial irradiation, and intracavitary irradiation. Other radiotherapeutic agents that are DNA damaging factors include microwaves and UV-irradiation. These factors effect a broad range of damage on DNA, on the precursors of DNA, on the replication and repair of DNA, and on the assembly and maintenance of chromosomes. Other approaches to radiation therapy are also contemplated in the present invention.

Such techniques may comprise intraoperative irradiation, in which a large dose of external radiation is directed at the tumor and surrounding tissue during surgery; and particle beam radiation therapy which involves the use of fast-moving subatomic particles to treat localized cancers. Radiotherapy may further involve the use of radiosensitizers and/or radioprotectors to increase the effectiveness of radiation therapy. Radiolabeled antibodies may also be used to deliver doses of radiation directly to the cancer site, this is known as radioimmunotherapy.

Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Surgery

Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery. It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by administration of an additional anti-cancer therapy, more particularly a TLR3 agonist. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Hormonal Therapy

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, or inhibitors of cell adhesion. Immunomodulatory agents include tumor necrosis factor; interferon alpha, beta, and gamma; IL-2, IL-12, IL-15, IL-21 and other cytokines; F42K and other cytokine analogs; or MIP-1, MIP-1 beta, MCP-1, RANTES, and other chemokines.

The treatment with a TLR3 agonist, and more particularly dsRNA molecule, may be accomplished as disclosed in the literature cited above. Furthermore, the treatment may be performed either alone or in combination with other drugs or treatments. The treatment may include a reduction in tumor size, a reduction or delay in tumor growth, development or metastasis, or a regression of cancer.

Thus, various non-limiting embodiments as set forth herein include:

1. The use of a TLR3 agonist for the manufacture of a medicament for treating cancer in a subject, wherein said cancer in said subject comprises cancer cells expressing a TLR3 receptor;

2. A method for assessing the response of a subject having cancer to a treatment using a TLR3 agonist, the method comprising determining whether cancer cells in said subject express a TLR3 receptor, the expression of a TLR3 receptor being indicative of a responder subject;

3. A method for selecting subjects having a cancer that respond to a treatment using a TLR3 agonist, the method comprising determining whether cancer cells in said subject express a TLR3 receptor, the expression of a TLR3 receptor being indicative of a responder subject;

4. A method for treating a subject having a cancer, the method comprising determining whether cancer cells in said subject express a TLR3 receptor, the expression of a TLR3 receptor being indicative of a subject responding to a TLR3 agonist, and treating said subject whose cancer cells express a TLR3 receptor with a double-stranded RNA molecule;

5. A use or method of any one of the preceding embodiments, wherein the subject is a human subject;

6. A use or method of any one of the preceding embodiments, wherein the cancer is a solid tumor and carcinoma;

7. The use or method of embodiment 6, wherein the solid tumor is selected from breast cancer, colon cancer, lung cancer, renal cancer, metastatic or invasive malignant melanoma, prostate cancer, brain tumor, bladder cancer and liver cancer;

8. The use or method of any one of the preceding embodiments, wherein the expression of a TLR3 receptor in said cancer cell is determined using a TLR3-specific ligand;

9. The use or method of embodiment 8, wherein the ligand is an antibody, or a fragment or derivative thereof;

10. The use or method of any one of embodiments 1 to 7, wherein the expression of a TLR3 receptor in said cancer cell is determined using a TLR3-specific primer or probe;

11. The use or method of any one of the preceding embodiments, wherein the expression of a TLR3 receptor in said cancer cell is determined in vitro or ex vivo;

12. The use or method of any one of the preceding embodiments, wherein the TLR3 agonist is a double-stranded RNA molecule;

13. The use or method of embodiment 12, wherein the double-stranded RNA molecule is a polyA/polyU molecule;

14. The use or method of embodiment 12, wherein the double-stranded RNA molecule is a polyI/polyC molecule;

15. The use of a double-stranded polyA/polyU RNA molecule for the manufacture of a medicament for treating breast cancer in a subject, wherein said breast cancer in said subject comprises cancer cells expressing a TLR3 receptor;

16. A kit for selecting subjects that respond to a treatment using a TLR3 agonist, the kit comprising reagents for determining the expression of a TLR3 receptor in a cancer cell in a sample; or 17. The kit of embodiment 16, wherein the TLR3 agonist is a double-stranded RNA molecule.

Further aspects and advantages of this invention will be disclosed in the following examples, which should be regarded as illustrative and not limiting the scope of this invention.

EXAMPLES

Toll like receptor 3 (TLR3) is known to be expressed by myeloid dendritic cells (DC) and to induce their maturation following binding with double stranded RNA (dsRNA) or its synthetic homologues polyAU and polyI:C. Several clinical trials have reported that injection of dsRNA is associated with survival benefit in cancer patients. In the present study, the inventors have asked whether dsRNA could act directly on tumor cells through TLR3. Patients and methods: 300 patients with early breast cancer have been included from 1972 to 1979 in a randomized trial comparing post-operative administration of polyAU with no treatment. Results have been reported that showed a trend for a survival benefit in patients with involved auxiliary lymph nodes (n=200).

Tumor biopsies from these patients were stained with TLR3-specific mAb and correlation between TLR3 expression and polyAU efficacy was determined.

To investigate directly the effects of dsRNA, both freshly isolated breast tumor cells and cancer cell lines were cultured with polyI:C, and apoptosis was measured. The involvement of TLR3 in cell response was established by TLR3 RNA interference.

Results: 182 tumor samples (91%) were available from the 200 pTxN+MO patients included in this randomized trial. TLR3 was strongly expressed by tumor cells in 18 patients (10%). Table 1 reports the 20-year survival rates according to treatment and TLR3 expression.

Targeting Toll Like Receptor 3 in Breast Cancer: Results of Randomized Trial and in vitro Studies Material and Methods Patients 200 patients were included in the present study. All patients had been previously included in a prospective randomized trial that compared double stranded RNA (polyAU) to placebo. This trial has already been reported elsewhere. Briefly, this randomized trial included patients with T1-3N0-3M0 breast cancer treated with surgery. Treatment consisted in weekly iv injection of polyAU (Beaufour Ipsen). A total of 6 injections were performed. PolyAU was administered at a fixed dose of 60 mg/injection. This trial initially included 300 patients. Since initial results of the trial reported a trend for benefit only in patients with auxiliary lymph node involvement, only the 200 patients with auxiliary node involvement were included in the present study.

Immunostainings

Tumor blocks were available in 182 out of 200 patients included in the present study. Paraffin-embedded, 5 um-thick tissue section from all 182 tumors were stained with either polyclonal antiTLR3 (gift from Dr Pobolsky, Massachusetts General Hospital, Boston) or rabbit preimmune serum. A mouse monoclonal anti-rabbit IgG was used as secondary antibody. Immunostainings were assessed by 2 pathologists who were blinded for clinical files. The TLR3 expression was classified according to the percentage of tumor cells stained and the intensity of staining. A tumor was classified as positive when more than 10% of tumor cells were strongly stained with the anti-TLR3 antibody.

Statistics

Survival curves were determined according to Kaplan-Meier method. Survival curves were compared using Khi2 test.

Results

Patients Characteristics

One hundred eighty two tumors were processed. The immunostaining could not be interpreted in 7 patients (absence of tumor cells in 4 patients, artefact in 3 patients). The analysis was therefore performed on 175 patients. This represents 87% of the patients included in the randomized trial. The median follow-up of living patients was 23 years (12 to 26 years). The patients characteristics are reported in Table 1. Briefly, the median age is 50, the median number of lymph node involved was 4 (1-31), 26% of tumor were staged pT3 and 35% were classified as grade III according to Scarf and Bloom Richardson.

TABLE 1

Patients characteristics

| Characteristics | TLR3− tumors (n = 157) | | TLR3+ tumors (n = 18) | | Total (n = 175) |
|---|---|---|---|---|---|
| | Observation (n = 77) | Poly AU (n = 80) | Observation (n = 10) | Poly AU (n = 8) | |
| Age (median) | 50 | 50 | 52 | 49 | 50 |
| Nb lymph node involved (median) | 5 (1-31) | 4 (1-27) | 2 (1-8) | 4 (1-9) | 4 (1-31) |
| pT | | | | | |
| pT1 | 8 | 1 | 0 | 0 | 9 |
| pT2 | 56 | 54 | 6 | 6 | 122 |
| pT3 | 13 | 27 | 4 | 2 | 46 |
| Tumor grade | | | | | |
| I | 11 | 9 | 1 | 2 | 23 |
| II | 34 | 49 | 6 | 3 | 92 |
| III | 32 | 24 | 3 | 3 | 62 |
| Post-operative radio-therapy | | | | | |
| Yes | 74 | 77 | 9 | 8 | 168 |
| No | 3 | 3 | 1 | 0 | 7 |

Immunostainings

TLR3 was strongly expressed by tumor cells in 18 samples (10.4% of assessable tumors). Immunostainings are shown in FIG. 1. TLR3 was mainly expressed on the cell surface and cytoplasm of tumor cells. In situ carcinoma and normal breast tissues were stained by anti-TLR3 in most cases. The patients characteristics of the TLR3+tumors did not differ to that of TLR3−tumors (Table 1).

Correlation Between TLR3 Expression and Survival After Treatment with polyAU

Figure 2A:
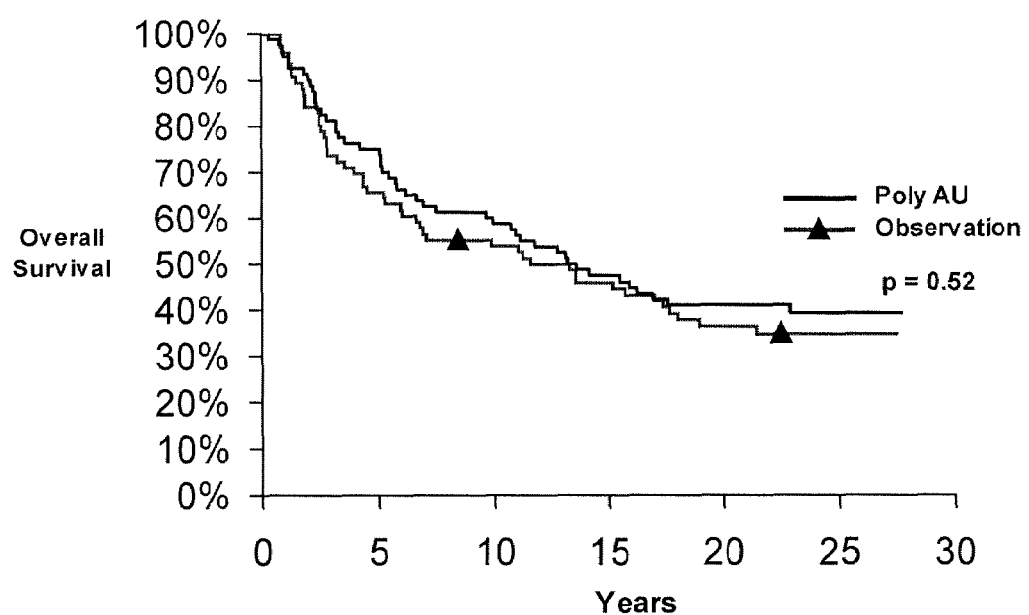
FIG. 2 illustrates survival of patients with TLR3−tumors (FIG. 2a) or with TLR3+tumors (FIG. 2b) according to treatment with a placebo (observation) or with dsRNA.
Figure 2B:
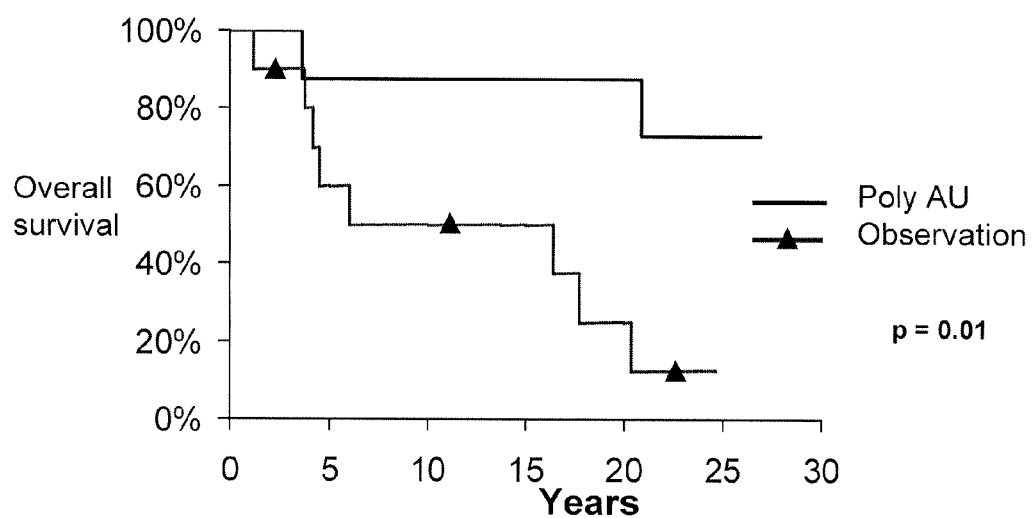

The 20 year OS of patients treated or not with polyAU were 42% and 35% respectively (p=0.09). When only patients with TLR3− tumors were considered, the 20 year OS were 41% for patients treated with polyAU, and 37% for those assigned to observation arm (p=0.52) (FIG. 2a). When only patients presenting TLR3+ tumors were considered, the 20 year OS were 88% for patients treated with polyAU, and 22% for patients assigned to the observation arm (p=0.01) (FIG. 2b).

CONCLUSION

TLR3 is overexpressed by tumor cells in around 10% of cancer cases.

TLR3 expression correlates with the benefit of adjuvant therapy with polyAU in patients with lymph node positive breast cancer.

The invention claimed is:

1. A method for assessing the responsiveness of a subject having breast cancer to treatment with a TLR3 agonist comprising determining whether breast cancer cells in said subject express a polypeptide comprising SEQ ID NO: 2, wherein the expression of SEQ ID NO: 2 on said breast cancer cells indicates that the subject will respond to treatment with polyA/polyU or polyI/polyC and the presence of SEQ ID NO: 2 on the surface of said breast cancer cells is determined using an antibody, or antigen binding fragment thereof, that specifically binds SEQ ID NO: 2 (TRL3) and said TLR3 agonist is a polyA/polyU molecule or a polyI/polyC molecule.

2. The method according to claim 1, wherein the expression of SEQ ID NO: 2 on said breast cancer cells is determined using an antibody that specifically binds to SEQ ID NO: 2.

3. The method according to claim 1, wherein the expression of a TLR3 receptor on said cancer cells is determined using an antigen binding fragment of an antibody that specifically binds to SEQ ID NO: 2.

4. The method according to claim 1, wherein the expression of SEQ ID NO: 2 on said breast cancer cells is determined in vitro or ex vivo.

5. A method for selecting a subject having breast cancer for treatment with a TLR3 agonist comprising determining whether breast cancer cells in a subject express a polypeptide comprising SEQ ID NO: 2 using an antibody, or antigen binding fragment thereof, that specifically binds SEQ ID NO: 2 (TLR3) and selecting said subject for treatment with a TLR3 agonist comprising polyA/polyU molecules or polyI/polyC molecules if said breast cancer cells express SEQ ID NO: 2.

6. The method according to claim 5, wherein the expression of a TLR3 receptor on said breast cancer cells is determined using an antibody that specifically binds to SEQ ID NO: 2.

7. The method according to claim 5, wherein the expression of SEQ ID NO: 2 on said breast cancer cells is determined using an antigen binding fragment of an antibody that specifically binds to SEQ ID NO: 2.

8. The method according to claim 5, wherein the expression of SEQ ID NO: 2 on said breast cancer cells is determined in vitro or ex vivo.

9. A method for treating a subject having a breast cancer comprising determining whether breast cancer cells in a sample obtained from a subject express a polypeptide comprising SEQ ID NO: 2 with an antibody, or antigen binding fragment thereof that specifically binds to SEQ ID NO: 2 and treating a subject whose cancer cells express a TLR3 receptor with a composition comprising a double-stranded RNA molecule comprising polyA/polyU or polyI/polyC.

10. The method according to claim 9, wherein the expression of SEQ ID NO: 2 on said breast cancer cells is determined using an antibody that specifically binds SEQ ID NO: 2.

11. The method according to claim 9, wherein the expression of SEQ ID NO: 2 on said breast cancer cells is determined using an antigen binding fragment of an antibody that specifically binds SEQ ID NO: 2.

12. The method according to claim 9, wherein the expression of SEQ ID NO: 2 on said breast cancer cells is determined in vitro or ex vivo.

* * * * *